United States Patent
Yu et al.

(10) Patent No.: US 12,338,232 B2
(45) Date of Patent: Jun. 24, 2025

(54) THRβ RECEPTOR AGONIST COMPOUND AND PREPARATION METHOD AND USE THEREOF

(71) Applicant: Terns, Inc., Foster City, CA (US)

(72) Inventors: Shanghai Yu, Kun Shan (CN); Ben Li, Kun Shan (CN)

(73) Assignee: Terns, Inc., Foster City, CA (US)

( * ) Notice: Subject to any disclaimer, the term of this patent is extended or adjusted under 35 U.S.C. 154(b) by 0 days.

(21) Appl. No.: 18/315,291

(22) Filed: May 10, 2023

(65) Prior Publication Data

US 2023/0278988 A1 Sep. 7, 2023

Related U.S. Application Data

(63) Continuation of application No. 17/951,883, filed on Sep. 23, 2022, now abandoned, which is a continuation of application No. 17/675,690, filed on Feb. 18, 2022, now abandoned, which is a continuation of application No. 17/305,302, filed on Jul. 2, 2021, now abandoned, which is a continuation of application No. 16/712,301, filed on Dec. 12, 2019, now Pat. No. 11,084,802.

(30) Foreign Application Priority Data

Dec. 13, 2018 (CN) .......................... 201811527414.4

(51) Int. Cl.
C07D 403/12 (2006.01)

(52) U.S. Cl.
CPC .................................. *C07D 403/12* (2013.01)

(58) Field of Classification Search
CPC .................................................. C07D 403/12
USPC ....................................................... 514/242
See application file for complete search history.

(56) References Cited

U.S. PATENT DOCUMENTS

| | | | |
|---|---|---|---|
| 4,197,307 A | 4/1980 | Gallay et al. | |
| 5,114,938 A | 5/1992 | Lindner et al. | |
| 6,787,652 B1 | 9/2004 | Dow et al. | |
| 7,807,674 B2 | 10/2010 | Haynes et al. | |
| 8,153,624 B2 | 4/2012 | Genin et al. | |
| 8,785,408 B2 | 7/2014 | Feinstein et al. | |
| 8,791,266 B2 | 7/2014 | Kawata et al. | |
| 10,208,019 B2 | 2/2019 | Aspnes et al. | |
| 10,800,767 B2 | 10/2020 | Kirschberg et al. | |
| 11,034,676 B2 | 6/2021 | Yu et al. | |
| 11,084,802 B2 | 8/2021 | Yu et al. | |
| 11,168,079 B2 | 11/2021 | Carpenter et al. | |
| 11,203,587 B2 | 12/2021 | Kirschberg et al. | |
| 11,964,964 B2 | 4/2024 | Jin et al. | |
| 2003/0078288 A1 | 4/2003 | Haning et al. | |
| 2004/0157844 A1 | 8/2004 | Dow et al. | |
| 2005/0085541 A1 | 4/2005 | Shiohara et al. | |
| 2008/0167313 A1 | 7/2008 | Dupont-Passelaigue et al. | |
| 2009/0005383 A1 | 1/2009 | Haynes et al. | |
| 2009/0247539 A1 | 10/2009 | Bell et al. | |
| 2010/0004271 A1 | 1/2010 | Garcia Collazo et al. | |
| 2010/0152166 A1 | 6/2010 | Genin et al. | |
| 2010/0286182 A1 | 11/2010 | Samuels et al. | |
| 2012/0129812 A1 | 5/2012 | Kawata et al. | |
| 2014/0275077 A1 | 9/2014 | Dandu et al. | |
| 2015/0368205 A1 | 12/2015 | Ji et al. | |
| 2017/0050949 A1 | 2/2017 | Dandu et al. | |
| 2017/0334883 A1 | 11/2017 | Albrecht et al. | |
| 2018/0297987 A1 | 10/2018 | Coates et al. | |
| 2019/0111012 A1 | 4/2019 | Hanf | |
| 2019/0247404 A1 | 8/2019 | Namisaki et al. | |
| 2019/0321364 A1 | 10/2019 | Satyal et al. | |
| 2019/0352286 A1 | 11/2019 | Claremon et al. | |
| 2020/0009092 A1 | 1/2020 | Roberts et al. | |
| 2020/0054589 A1 | 2/2020 | Noel et al. | |
| 2020/0062742 A1 | 2/2020 | Kirschberg et al. | |
| 2020/0115362 A1 | 4/2020 | Kirschberg et al. | |
| 2020/0190064 A1 | 6/2020 | Yu et al. | |
| 2020/0354345 A1 | 11/2020 | Vandyck et al. | |

(Continued)

FOREIGN PATENT DOCUMENTS

| | | |
|---|---|---|
| CN | 101228135 A | 7/2008 |
| CN | 102898377 A | 1/2013 |

(Continued)

OTHER PUBLICATIONS

Bashir, M., et al., "Liver vol. Reduction in Resmetirom Treated Non-Cirrhotic and Cirrhotic NASH Patients," Hepatology, Oct. 2021, vol. 74, No. 1 (Supplement), pp. 1142A-1143A.

(Continued)

*Primary Examiner* — Kahsay Habte
(74) *Attorney, Agent, or Firm* — COOLEY LLP

(57) ABSTRACT

The present invention discloses a compound represented by the following Formula (I) and a pharmaceutically acceptable salt thereof. The compound improves the THRα selectivity while maintaining good THRβ agonistic activity, thereby improving properties of the finished drug.

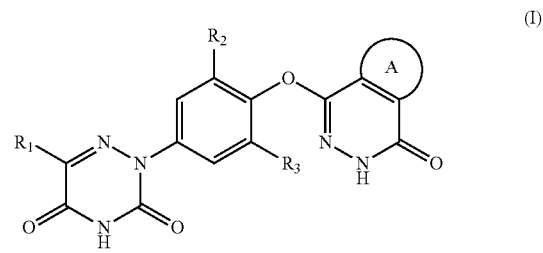

(I)

25 Claims, No Drawings

(56) References Cited

U.S. PATENT DOCUMENTS

| | | |
|---|---|---|
| 2020/0397798 A1 | 12/2020 | Mohan et al. |
| 2020/0399249 A1 | 12/2020 | Yu et al. |
| 2021/0115022 A1 | 4/2021 | Jin et al. |
| 2021/0379040 A1 | 12/2021 | Fenaux et al. |
| 2021/0379043 A1 | 12/2021 | Fenaux et al. |
| 2022/0135540 A1 | 5/2022 | Sweetana et al. |
| 2022/0281849 A1 | 9/2022 | Kirschberg et al. |
| 2022/0332707 A1 | 10/2022 | Du et al. |
| 2022/0348561 A1 | 11/2022 | Kirschberg et al. |
| 2022/0356177 A1 | 11/2022 | Kirschberg et al. |
| 2023/0241071 A1 | 8/2023 | Fenaux et al. |
| 2024/0000765 A1 | 1/2024 | Fenaux et al. |
| 2024/0059682 A1 | 2/2024 | Kirschberg et al. |
| 2024/0156826 A1 | 5/2024 | Taub |
| 2024/0239761 A1 | 7/2024 | Zhang et al. |
| 2024/0293416 A1 | 9/2024 | Jones et al. |
| 2024/0316025 A1 | 9/2024 | Fenaux et al. |

FOREIGN PATENT DOCUMENTS

| | | |
|---|---|---|
| CN | 103130723 A | 6/2013 |
| CN | 105477636 A | 4/2016 |
| CN | 110167557 A | 8/2019 |
| CN | 111320609 A | 6/2020 |
| CN | 111484481 A | 8/2020 |
| CN | 111909137 A | 11/2020 |
| CN | 114437034 A | 5/2022 |
| EP | 1471049 A1 | 10/2004 |
| EP | 3437659 A1 | 2/2019 |
| EP | 3807267 A1 | 4/2021 |
| IN | 202047050376 A | 4/2020 |
| JP | H02225483 A | 9/1990 |
| JP | 2001114768 A | 4/2001 |
| JP | 2004517851 A | 6/2004 |
| JP | 2007512314 A | 5/2007 |
| JP | 2009501759 A | 1/2009 |
| JP | 2011114768 A | 6/2011 |
| JP | 2011528007 A | 11/2011 |
| JP | 2017525740 A | 9/2017 |
| JP | 2021531325 A | 11/2021 |
| RU | 2668960 C2 | 10/2018 |
| WO | WO-0198256 A1 | 12/2001 |
| WO | WO-03064369 A1 | 8/2003 |
| WO | WO-03094845 A2 | 11/2003 |
| WO | WO-2007003419 A1 | 1/2007 |
| WO | WO-2007009913 A1 | 1/2007 |
| WO | WO-2007128492 A1 | 11/2007 |
| WO | WO-2007134864 A1 | 11/2007 |
| WO | WO-2009012125 A1 | 1/2009 |
| WO | WO-2009037172 A1 | 3/2009 |
| WO | WO-2010006962 A1 | 1/2010 |
| WO | WO-2010122980 A1 | 10/2010 |
| WO | WO-2011038207 A1 | 3/2011 |
| WO | WO-2014043706 A1 | 3/2014 |
| WO | WO-2016036873 A1 | 3/2016 |
| WO | WO-2017167935 A1 | 10/2017 |
| WO | WO-2017170434 A1 | 10/2017 |
| WO | WO-2018027892 A1 | 2/2018 |
| WO | WO-2018028517 A1 | 2/2018 |
| WO | WO-2018073154 A1 | 4/2018 |
| WO | WO-2018075650 A1 | 4/2018 |
| WO | WO-2018103624 A1 | 6/2018 |
| WO | WO-2018153933 A1 | 8/2018 |
| WO | WO-2018167103 A1 | 9/2018 |
| WO | WO-2018170173 A1 | 9/2018 |
| WO | WO-2018193006 A1 | 10/2018 |
| WO | WO-2018193007 A1 | 10/2018 |
| WO | WO-2018208707 A1 | 11/2018 |
| WO | WO-2019023245 A1 | 1/2019 |
| WO | WO-2019038456 A1 | 2/2019 |
| WO | WO-2019053233 A1 | 3/2019 |
| WO | WO-2019053235 A1 | 3/2019 |
| WO | WO-2019094777 A1 | 5/2019 |
| WO | WO-2019144835 A1 | 8/2019 |
| WO | WO-2019240938 A1 | 12/2019 |
| WO | WO-2020041741 A1 | 2/2020 |
| WO | WO-2020042114 A1 | 3/2020 |
| WO | WO-2020061086 A2 | 3/2020 |
| WO | WO-2020061114 A1 | 3/2020 |
| WO | WO-2020073974 A1 | 4/2020 |
| WO | WO-2020077123 A1 | 4/2020 |
| WO | WO-2020123827 A1 | 6/2020 |
| WO | WO-2020131578 A2 | 6/2020 |
| WO | WO-2020169069 A1 | 8/2020 |
| WO | WO-2020227549 A1 | 11/2020 |
| WO | WO-2020239076 A1 | 12/2020 |
| WO | WO-2021014350 A1 | 1/2021 |
| WO | WO-2021041237 A1 | 3/2021 |
| WO | WO-2021050945 A1 | 3/2021 |
| WO | WO-2021121210 A1 | 6/2021 |
| WO | WO-2021231644 A1 | 11/2021 |
| WO | WO-2021231646 A1 | 11/2021 |
| WO | WO-2022152770 A1 | 7/2022 |
| WO | WO-2022187403 A1 | 9/2022 |
| WO | WO-2023083288 A1 | 5/2023 |
| WO | WO-2023086561 A1 | 5/2023 |
| WO | WO-2023220404 A1 | 11/2023 |

OTHER PUBLICATIONS

Co-pending U.S. Appl. No. 18/818,705, inventors Kirschberg; Thorsten A. et al., filed Aug. 29, 2024.

Dennis, A., et al., "Correlations Between MRI Biomarkers PDFF and cT1 with Histopathological Features on Non-Alcoholic Steatohepatitis," Frontiers in Endocrinology, Jan. 2021, vol. 11, Article 575843, 10 pages.

Extended European Search Report and Search Opinion, dated Apr. 2, 2024, for European Patent Application No. 21803928.7, 11 pages.

Gallup. Americans' Average Weight Holds Steady in 2020, Jan. 4, 2021, Retrieved from the Internet on Sep. 27, 2023, https://news.gallup.com/poll/328241/americans-average-weight-holds-steady-2020.aspx, 9 pages.

Harrison, S. A., et al., "A Phase 3, Randomized, Controlled Trial of Resmetirom in NASH with Liver Fibrosis," The New England Journal of Medicine, Feb. 8, 2024, vol. 390, No. 6, pp. 497-509.

Harrison, S. A., et al., "Resmetirom for nonalcoholic fatty liver disease: a randomized, double-blind, placebo-controlled phase 3 trial," Nature Medicine, Nov. 2023, vol. 29, 2919-2928, including additional material, 19 pages, DOI: 10.1038/s41591-023-02603-1.

International Preliminary Report on Patentability for International Application No. PCT/US2022/049690 mailed May 23, 2024, 12 pages.

International Preliminary Report on Patentability, mailed May 23, 2024, for International Application No. PCT/CN2022/131297, 7 pages.

Kirschberg, T., et al., "TERN-501, a potent and selective agonist of thyroid hormone receptor beta, strongly reduces histological features and biomarkers of non-alcoholic steatohepatitis associated pathology in rodent models," Journal of Hepatology 2020, vol. 73, S653-S915, p. S684, SAT066.

Loomba, R., et al., Relationship of Non-Invasive Measures with Histological Response in Patients with NonAlcoholic Steatohepatitis and Fibrosis: 52-Week Data from the Phase 3 Maestro-NASH Trial, Hepatology, 2023, 78 (Supplement 1):S155-S159, Abstract 149.

Noureddin, M., et al., "5000 | Topline Results from a 12-Week Phase 2a Trial (Duet) Evaluating Tern-501, A Highly Selective Thyroid Hormone Receptor (THR) Beta Agonist, Either as Monotherapy or in Combination with TERN-101, A Nonsteroidal Farnesoid X Receptor (FXR) Agonist, Demonstrated Significant Reductions in MR-Based Liver Fat Content and Fibroinflammation in Patients with Presumed MASH," Hepatology 2024, 79:E33-E85, p. E33.

Noureddin, M., et al., "Head-to-Head Comparison of Fast, Mast, MEFIB and cT1 in Identifying At-Risk NASH Patients in a Low-Prevalence Population," Hepatology, 2023, 78(Supplement 1):S1-S2154, pp. S806-S810, Abstract 2050-A.

Rich, N. E., et al., "Racial and Ethnic Disparities in Nonalcoholic Fatty Liver Disease Prevalence, Severity, and Outcomes in the

(56) References Cited

OTHER PUBLICATIONS

United States: A Systematic Review and Meta-analysis," Clinical Gastroenterology and Hepatology 2018, 16, 198-210, 210.e1-210.e2.

Rinella, M. E., et al., "AASLD Practice Guidance on the clinical assessment and management of nonalcoholic fatty liver disease," Hepatology 2023, 77, 1797-1835.

Stine, J. G., et al., "Change in MRI-PDFF and Histologic Response in Patients with Non-alcoholic Steatohepatitis: A Systematic Review and Meta-Analysis," Clinical Gastroenterology and Hepatology 2021, vol. 19, No. 11, 2274-2283, 2283.e1-2283.e5.

Sumida, Y., et al., "Current and new pharmacotherapy options for non-alcoholic steatohepatitis," Expert Opinion on Pharmacotherapy, vol. 21, No. 8, Apr. 1, 2020, pp. 953-967, DOI: 10.1080/14656566.2020.1744564.

Ashburner M., et al., "Gene Ontology: Tool For The Unification Of Biology. The Gene Ontology Consortium," Nature Genetics, May 2000, vol. 25, pp. 25-29.

Basnak, I. et al. (1975). "Synthesis of 5-cyclopropyl-6-azauracil," Collect. Czech Chem. Commun. 40(4):1038-1042.

Baxter, J. D. et al., "Thyroid hormone mimetics: potential applications in atherosclerosis, obesity and type 2 diabetes," Nature Reviews Drug Discovery, vol. 8, No. 4, pp. 308-320 (Apr. 2009).

Belikov, V.G, "Pharmaceutical Chemistry. Chapter 2.6 Relationship between the chemical structure, properties of substances and their effect on the body", MEDpress-inform (2007); pp. 27-29; 14 pages with English translation.

Berry, M. J., et al., "Thyroid hormone regulates type I deiodinase messenger RNA in rat liver," Molecular Endocrinology, 1990, 4:743-748.

Brecher, J., "Graphical Representation of Stereochemical Configuration (IUPAC Recommendations 2006)," Pure and Appl. Chem. 78(10):1897-1970 (2006).

Chen, H.C. et al. (Nov. 13-16, 2020). MET409, an Optimized Sustained FXR Agonist, Was Safe and Well-Tolerated in a 14-Day Phase 1 Study in Healthy Subjects, Me0.tacrine, 1 page, Poster presented at Poster presentation at EASL—The International Liver Congress, Apr. 2019, Vienna, Austria.

Chung D., et al., "Pharmacokinetics Of Two Oral Formulations Of Liver-directed, Nonsteroidal Farnesoid X-Receptor Agonist Tern-101 In Healhy Volunteers," Terns Pharmaceutical, Inc., Poster presented at Paris NASH Meeting, Oct. 22-23, 2020, 1 Page.

Dermer, G.B., "Another Anniversary for the War on Cancer," Bio/Technology, 12:320, 1 page (Mar. 1994).

Dufour J-F., et al., "Combination Therapy For Non-Alcoholic Steatohepatitis: Rationale, Opportunities And Challenges," Gut, 69(10):1877-1884 (2020).

Dunkel, P. et al., "Semicarbazide-sensitive amine oxidase/vascular adhesion protein-1: a patent survey," Expert Opinion on Therapeutic Patents, Jun. 2011, vol. 21, No. 9, pp. 1453-1471, doi: 10.1517/13543776.2011.594040.

Erion, M.D., "Targeting thyroid hormone receptor-β agonists to the liver reduces cholesterol and triglycerides and improves the therapeutic index," PNAS, Sep. 25, 2007, 104(39), 15490-15495.

Extended European Search Report and Search Opinion for Application No. 19870196.3, mailed on May 18, 2022, 5 pages.

Extended European Search Report and Search Opinion for European Application No. 19852050.4, mailed Mar. 22, 2022, 7 Pages.

Extended European Search Report and Search Opinion, mailed Aug. 17, 2023, for European Patent Application No. 20863146.5, 7 pages.

Extended European Search Report and Search Opinion, mailed Jul. 6, 2022, for European Application No. 19896475.1 (8 total pages).

Extended European Search Report and Search Opinion, mailed Mar. 30, 2023, for European Application No. 20856291.8 (8 total pages).

Fiorucci, S., et al., "Future trends in the treatment of nonalcoholic steatohepatitis," Pharmacological Research, Jul. 2018, vol. 134, pp. 289-298, doi: 10.1016/J.PHRS.2018.07.014.

Freshney R.I., et al., "Culture of Animal Cells," A Manual of Basic Technique, 1983, Alan R. Liss, Inc., New York, p. 4 and pp. 129-133 (9 total pages).

Gene Ontology Consortium, Creating the Gene Ontology Resource: Design and Implementation. Genome Research 11: 1425-1433 (2001).

Grover, G. J., et al., Effects of the thyroid hormone receptor agonist GC-1 on metabolic rate and cholesterol in rats and primates: selective actions relative to 3,5,3'-triiodo-L-thyronine, Endocrinology, vol. 145, No. 4, pp. 1656-1661 (Apr. 2004).

Han C.Y., "Update on FXR Biology: Promising Therapeutic Target?," International Journal of Molecular Sciences, Jul. 16, 2018, vol. 19, No. 2069, 25 pages.

Hansen, H. H., et al., "Human translatability of the GAN diet-induced obese mouse model of non-alcoholic steatohepatitis," BMC Gastroenterology (2020), 20:210, pp. 1-12, https://doi.org/10.1186/s12876-020-01356-2.

Hennessey, J. V., et al., "The emergence of levothyroxine as a treatment for hypothyroidism," Endocrine, 2017, 55: 6-18, DOI: 10.1007/s12020-016-1199-8.

Hill, S. R. Jr., S et al. (1960). "The Metabolic Effects of the Acetic and Propionic Acid Analogs of Thyroxine and Triiodothyronine," J Clin. Invest. (39):523-533.

Ichiki, T., et al., "Thyroid Hormone and Vascular Remodeling," Journal of Atherosclerosis and Thrombosis, 2016, vol. 23, No. 3, pp. 266-275.

International Preliminary Report on Patentability for International Application No. PCT/CN2018/103349, mailed Mar. 11, 2021, 7 Pages.

International Preliminary Report on Patentability for International Application No. PCT/US2008/069719, mailed Jan. 19, 2010, 7 Pages.

International Preliminary Report on Patentability for International Application No. PCT/US2019/047968, mailed Mar. 11, 2021, 7 Pages.

International Preliminary Report on Patentability for International Application No. PCT/US2019/055689, mailed Apr. 22, 2021, 9 Pages.

International Preliminary Report on Patentability for International Application No. PCT/US2019/066013, mailed Jun. 24, 2021, 6 Pages.

International Preliminary Report on Patentability for International Application No. PCT/US2020/047467, mailed Mar. 3, 2022, 9 Pages.

International Preliminary Report on Patentability for International Application No. PCT/US2020/050497, mailed Mar. 24, 2022, 7 Pages.

International Preliminary Report on Patentability for International Application No. PCT/US2022/018575, mailed Sep. 14, 2023, 18 pages.

International Preliminary Report on Patentability, mailed Nov. 24, 2022, for International Application No. PCT/US2021/032085 (12 total pages).

International Search Report and Written Opinion for International Application No. PCT/CN2018/103349, mailed Jun. 5, 2019, 9 Pages.

International Search Report and Written Opinion for International Application No. PCT/CN2022/131297, mailed on Feb. 10, 2023, 10 pages.

International Search Report and Written Opinion for International Application No. PCT/US2008/069719, mailed Nov. 6, 2008, 9 Pages.

International Search Report and Written Opinion for International Application No. PCT/US2019/047968, mailed Nov. 21, 2019, 9 Pages.

International Search Report and Written Opinion for International Application No. PCT/US2019/055689, mailed Jan. 23, 2020, 12 Pages.

International Search Report and Written Opinion for International Application No. PCT/US2019/066013, mailed Feb. 28, 2020, 8 Pages.

International Search Report and Written Opinion for International Application No. PCT/US2020/047467, mailed Jan. 15, 2021, 12 Pages.

(56) References Cited

OTHER PUBLICATIONS

International Search Report and Written Opinion for International Application No. PCT/US2020/050497, mailed Dec. 8, 2020, 9 Pages.
International Search Report and Written Opinion for International Application No. PCT/US2020/059522, mailed Feb. 5, 2021, 9 Pages.
International Search Report and Written Opinion for International Application No. PCT/US2021/032085, mailed Sep. 30, 2021, 17 Pages.
International Search Report and Written Opinion for International Application No. PCT/US2022/049690, mailed Mar. 16, 2023, 21 pages.
International Search Report and Written Opinion, mailed Aug. 2, 2023, for International Application No. PCT/US2023/022093, 8 pages.
International Search Report and Written Opinion, mailed May 23, 2022, for International Application No. PCT/US2022/018575 (21 total pages).
Invitation to Pay Additional Fees, and, Where Applicable, Protest Fee, mailed Jul. 6, 2021, for International Application No. PCT/US2021/032083 (3 total pages).
Invitation to Pay Additional Fees, mailed Jul. 6, 2021, for International Application No. PCT/US2021/032085, 3 pages.
Invitation to Pay Additional Fees, mailed Nov. 21, 2019, for International Application No. PCT/US2019/055689, 2 pages.
Invitation to Pay Additional Fees, mailed Oct. 4, 2020, for International Application No. PCT/US2020/047467, 2 pages.
Jones C., et al., "Combination of TERN-101, a Farnesoid X Receptor Agonist, and TERN-501, a Selective Agonist of Thyroid Hormone Receptor Beta, Reduces Activation of Inflammatory and Fibrotic Gene Pathways in a Mouse Model of Non- Alcoholic Steatohepatitis," Terns Pharmaceuticals, Poster No. 0517, Poster Presented AASLD The Liver Meeting, Foster City, Nov. 13-16, 2020, 1 Page.
Jones, C., et al., EASL, Aug. 28, 2020, Single doses of TERN-201, a novel selective semicarbazide-sensitive amine oxidase (SSAO) inhibitor, are safe, well-tolerated, and result in sustained reduction of SSAO activity in healthy participants, Poster, 1 page.
Jones, C., et al., Single doses of the THR-B agonist TERN-501 are well tolerated and result in dose-dependent changes in LDL cholesterol and sex hormone binding globulin in a first-in-human clinical trial, AASLD, Nov. 12-15, 2021, Poster No. 1889, 1 page.
Kawamata, Y., et al. "AG protein-coupled receptor responsive to bile acids", The Journal of Biological Chemistry, 278(11):9435-9440 (Mar. 2003).
Kelly, M. J., et al., "Discovery of 2-[3,5-Dichloro-4-(5-isopropyl-6-oxo-1,6-dihydropyridazin-3-yloxy)phenyl]-3,5-dioxo-2,3,4,5-tetrahydro[1,2,4]triazine-6- carbonitrile (MGL-3196), a Highly Selective Thyroid Hormone Receptor β Agonist in Clinical Trials for the Treatment of Dyslipidemia," Journal of Medicinal Chemistry, 2014, 57, 10, 3912-3923, https://doi.org/10.1021/jm4019299.
Kim D., et al., "Critical Roles of the Histone Methyltransferase MLL4/KMT2D in Murine Hepatic Steatosis Directed by ABL1 and PPARgamma2," Cell Reports, 2016, vol. 17(6), pp. 1671-1682, DOI: 10.1016/j.celrep.2016.10.023.
Kirschberg, T., et al., EASL, Aug. 29, 2020, "TERN-501, a potent and selective agonist of thyroid hormone receptor beta, strongly reduces histological features and biomarkers of non-alcoholic steatohepatitis associated pathology in rodent models," poster, 1 page.
Klein, I et al., "Cardiovascular Involvement in General Medical Conditions, Thyroid Disease and the Heart," Circulation, Oct. 9, 2007, 116:1725-1735.
Kleiner, D. E., et al., "Design and validation of a histological scoring system for nonalcoholic fatty liver disease," Hepatology, Jun. 2005, 41(6):1313-1321.
Klucher, K., et al., EASL, Aug. 29, 2020, Anti-inflammatory and anti-fibrotic activity of TERN-201, a semicarbazide-sensitive amine oxidase inhibitor, in a rat choline-deficient high-fat diet non-alcoholic steatohepatitis model, Poster, 1 page.
Kogler, M., "Synthesis and Evaluation of 6-aza-2'-deoxyuridine Monophosphate Analogs as Inhibitors pf Thymidylate Synthases, and as Substrates or Inhibitors of Thymidine Monophosphate Kinase in Mycobacterium tuberculosis," Chemistry & Biodiversity, vol. 9 (2012), pp. 536-556.
Kowalik et al., "Thyroid Hormones, Thyromimetics and Their Metabolites in the Treatment of Liver Disease," Frontiers in Endocrinology, vol. 9, Article 382, pp. 1-11 (Jul. 2018).
Krchnak, V. et al., "Novel Pyrimidine Derivatives, Reactions and Ultraviolet Spectra," Collection Czechoslov. Chem. Commun. 1975, vol. 40, pp. 1396-1402.
Kremoser C., "Fxr Agonists for NASH: How Are They Different And What Difference Do They Make?," Journal of Hepatology 2021, vol. 75, pp. 12-15.
Liver Meeting Digital Experience 2020, Oct. 14, 2020, https://www.ternspharma.com/1 0-14-20- terns-to-present-positive-data-on-single-agend-and-combo-nash-at-liver-meeting-exp-2020, 3 pages.
Loomba, R., et al., "Nonalcoholic fatty liver disease progression rates to cirrhosis and progression of cirrhosis to decompensation and mortality: a real world analysis of Medicare data," Alimentary Pharmacology and Therapeutics, 2020, 51:1149-59, DOI: 10.1111/apt.15679.
Nelson, C. H., et al., Multiple Doses of Thyroid Hormone Receptor-Beta Agonist TERN-501 were Well-Tolerated and Resulted in Significant Dose-Dependent Changes in Serum Lipids and Sex Hormone Binding Globulin in a First-in-Human Clinical Study, EASL, Presentation, Abstract No. OS123, Jun. 25, 2022, 18:15-18-30, 17 pages.
Nelson, C. H., et al., Thyroid Hormone Beta Receptor Agonist Tern-501 Demonstrates Dose- And Exposure-Dependent Increases In Sex Hormone Binding Globulin With Associated Decreases In Atherogenic Lipids In Healthy Subjects, AASLD The Liver Meeting, Nov. 4-8, 2022, poster, 1 page.
Nelson, R. H., "Hyperlipidemia as a risk factor for cardiovascular disease," Prim Care Clin Office Pract 40 (2013) 195-211, http://dx.doi.org/10.1016/j.pop.2012.11.003.
Obach R.S., et al., "The Prediction Of Human Pharmacokinetic Parameters From Preclinical And In Vitro Metabolism Data," Journal of Pharmacology and Experimental Therapeutics, 1997, vol. 283, No. 1, pp. 46-58.
Pagadala, M. R, et al., "Prevalence of hypothyroidism in nonalcoholic fatty liver disease," Digestive Diseases and Sciences, 2012, 57:528-534, DOI 10.1007/s10620-011-2006-2.
Pubchem (Jan. 12, 2016). "4-(1,2,4-Benzotriazin-3-Yloxy)-N-Methylaniline," CID: 103204817, 7 pages.
Schwimmer, J. B., et al., "Prevalence Of Fatty Liver In Children And Adolescents," Pediatrics, Oct. 2006, vol. 118, No. 4, pp. 1388-1393.
Shepherd, E. L., et al., "Inhibition Of Vascular Adhesion Protein-1 Modifies Hepatic Steatosis In Vitro And In Vivo," World Journal of Hepatology, Nov. 27, 2020, vol. 12, No. 11, pp. 931-948.
Simone, J. V. (1996) "Introduction" in Cecil Textbook of Medicine. 20th Ed., vol. I . J. Claude Bennet and F. Plum (Eds.) W.B. Sauders Co.; pp. 1004-1010.
Sinha, R. A. et al., "Direct Effects of Thyroid Hormones on Hepatic Lipid Metabolism," Nat. Rev. Endocrinology, May 2018, 14(5):259-269 (26 total pages).
Taub, R,, et al., 'Lipid lowering in healthy volunteers treated with multiple doses of MGL-3196, a liver-targeted thyroid hormone receptor-β agonist,' Atherosclerosis, 2013, 230:373-380.
U.S. Appl. No. 17/305,302, filed Jul. 2, 2021, by Shanghai Yu et al. (The U.S. Patent Application is not submitted herewith pursuant to the waiver of 37 C.F.R. § 1.98(a)(2)(iii) issued by the Office on Sep. 21, 2004.).
Vuppalanchi, R., et al., "Therapeutic pipeline in nonalcoholic steatohepatitis," Nature Reviews Gastroenterology, Feb. 2021, vol. 18, No. 6, pp. 373-392, doi: 10.1038/S41575-020-00408-Y.
Walenbergh, S. A., et al., "Cholesterol is a significant risk factor for nonalcoholic steatohepatitis," Expert Review of Gastroenterology & Hepatology 2015, 9(11):1343-1346.

(56) References Cited

OTHER PUBLICATIONS

Extended European Search Report and Search Opinion, dated Dec. 23, 2024, for European Patent Application No. 22764006.7, 10 pages.

International Preliminary Report on Patentability, mailed Nov. 28, 2024, for International Application No. PCT/US2023/022093, 6 pages.

THRβ RECEPTOR AGONIST COMPOUND AND PREPARATION METHOD AND USE THEREOF

CROSS-REFERENCE TO RELATED APPLICATIONS

This application is a continuation of U.S. patent application Ser. No. 17/951,883, filed Sep. 23, 2022, which is a continuation of U.S. patent application Ser. No. 17/675,690, filed Feb. 18, 2022, now abandoned, which is a continuation of U.S. patent application Ser. No. 17/305,302, filed Jul. 2, 2021, now abandoned, which is a continuation of U.S. patent application Ser. No. 16/712,301, filed Dec. 12, 2019, now U.S. Pat. No. 11,084,802, which claims priority to Chinese Patent Application No. 201811527414.4, filed Dec. 13, 2018, the disclosures of which are hereby incorporated by reference in their entirety for all purposes.

TECHNICAL FIELD

The present invention relates to the field of pharmaceutical syntheses, and particularly to a compound that can serve as a novel agonist of THRβ receptors, and a preparation method and use thereof.

BACKGROUND

Thyroid hormone (TH) is synthesized in the thyroid gland in response to the thyroid stimulating hormone (TSH) secreted by the pituitary. Thyroxine plays a rather important role in regulating body growth, development, metabolism, and body balance. Thyroid hormones mainly include two types: 3,5,3'-triiodo-L-thyroxine (T3) and thyroxine (T4). Human bodies mainly secrete T4. In peripheral organs, T4 is transformed by deiodinase into T3 having greater activity. T3 and T4 produced by the thyroid gland are under negative feedback control. Thyrotropin (TSH) is responsible for the normal thyroid function and thyroid hormone secretion. Thyrotropin is synthesized in the anterior pituitary gland, and its secretion is controlled by the thyroid releasing hormone (TRH) synthesized in the hypothalamus.

Thyroid hormones function by binding to the thyroid hormone receptors (THR). The thyroid hormone receptor belongs to a family of nuclear receptors and regulates the target gene expressions. Thyroid hormone receptors include two different subtypes, i.e., THRα and THRβ. THRα is mainly distributed in cardiac tissues and plays an important role in regulating heart function. The THRβ subtype is mainly expressed in the liver and the pituitary, and regulates cholesterol metabolism and thyrotropin secretion.

At normal levels, thyroid hormones THs maintain body weight, metabolic rate, body temperature, and mood, and are responsible for regulating serum cholesterol. Attempts have been made to use thyroid hormones to regulate serum cholesterol. However, given the possible side effects on the heart from taking natural thyroid hormone (e.g., tachycardia and arrhythmia, heart failure, and thyroid axis function, muscle metabolism, and osteoporosis,) thyroid hormones are unsuitable for treating high cholesterol and obesity. Research results regarding the study of animals with selective knock-out of the THR gene, and research results of some selective THR ligands show that the side effects on the heart caused by these thyroid hormones can be attributed to THRα.

The pathway of the thyroid hormone receptor regulates metabolism of lipids, including cholesterol, triglyceride, and lipoprotein. It has been clinically shown that lowering the low-density cholesterol can reduce the incidence of cardiovascular diseases.

Non-alcoholic fatty liver disease (NAFLD) is also a type of metabolic disorder disease caused by excessive accumulation of triglycerides in the liver, which can further cause liver cell damage and inflammation, leading to non-alcoholic steatohepatitis (NASH). NASH patients usually have type 2 diabetes, high cholesterol, hyperlipaemia, and obesity along with NASH. Furthermore, they are more likely to develop hepatocirrhosis, liver failure and, eventually, liver cancer. In the field, currently drugs that effectively treat NASH are limited. Given the thyroid hormone's function of regulating the lipid metabolism, the thyroid receptor pathway becomes a potential target for the treatment of NASH and NAFLD. It has been proven in animal bodies that thyroid hormone analogues can significantly reduce fatty levels in animal livers.

Selective THRβ agonists can be used to avoid side effects on the heart that result from conventional THR receptor agonists, and selectively to only activate THRβ, thereby improving cell lipid metabolism, and achieve the function of lowering cholesterol and blood fat. However, selective THRβ agonists may also inhibit the thyroid axis, leading to depression, fatigue, osteoporosis, and other side effects. Therefore, it is desired to develop a selective THRβ agonist to activate THRβ, but to also reduce the inhibition of the thyroid axis, so as to avoid the side effects accompanying the thyroid axis inhibition.

Patents such as WO03094845, WO2007009913, WO2010122980, and WO2011038207 reveal some THR receptor agonists. Structures of these agonists are almost all designed and developed based on the natural ligand T3 of the THR receptor. Based on such background, it is still desired to develop selective THRβ receptor agonists which not only have the beneficial therapeutic effects of thyroid hormones, but also avoid side effects affecting the heart.

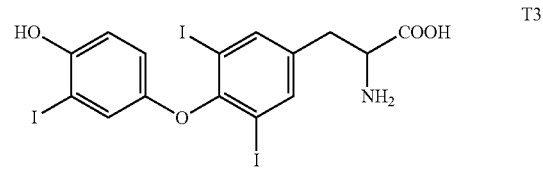 [SMILES: NC(Cc1cc(I)c(Oc2ccc(O)c(I)c2)c(I)c1)C(=O)O]

T3

Structural modification is carried out in the present invention also on the basis of the natural ligand T3 of the THR receptor. The present inventors unexpectedly found that, most of the modified compounds maintain good agonistic activity toward the THRβ receptor, and some compounds also have improved selectivity toward THRα as compared with Comparative compound 53 in the reference documents ("Discovery of 2-[3,5-Dichloro-4-(5-isopropyl-6-oxo-1,6-dihydropyridazin-3-yloxy)phenyl]-3,5-dioxo-2,3,4,5-tetrahydro[1,2,4]triazine-6-carbonitrile (MGL-3196), a Highly Selective Thyroid Hormone Receptor β Agonist in Clinical Trials for the Treatment of Dyslipidemia," Martha et al., *Journal of Medicinal Chemistry*, 2014, 3912-3923). At the same time, some compounds of the present invention also show very desirable pharmacokinetic properties. The pharmacokinetic properties of some preferred compounds are significantly better than those of the comparative compound, thus improving the properties of the finished drug.

Comparative Compound 53

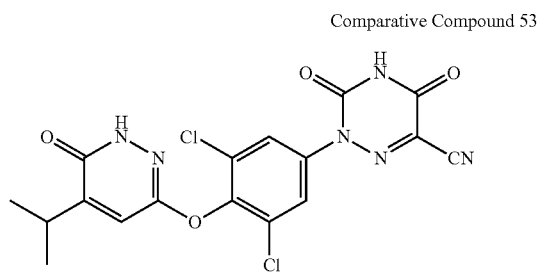 [SMILES: CC(C)c1cc(Oc2c(Cl)cc(-n3nc(C#N)c(=O)[nH]c3=O)cc2Cl)n[nH]c1=O]

SUMMARY

In order to solve the above technical problem, the present invention employs the following technical solutions:

According to one aspect of the present invention, the present invention provides a compound represented by the following Formula (I) and a pharmaceutically acceptable salt thereof,

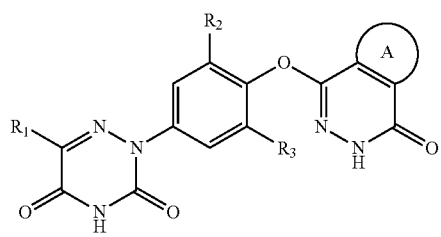

(I)

wherein, $R_1$ is selected from the group consisting of hydrogen, cyano, substituted or unsubstituted $C_{1-6}$ alkyl, or substituted or unsubstituted $C_{3-6}$ cycloalkyl, the substituent being selected from the group consisting of halogen atoms, hydroxy, and $C_{1-6}$ alkoxy;

$R_2$ and $R_3$ are each independently selected from the group consisting of halogen atoms or substituted or unsubstituted $C_{1-6}$ alkyl, the substituent being selected from the group consisting of halogen atoms, hydroxy, and $C_{1-6}$ alkoxy;

ring A is a substituted or unsubstituted saturated or unsaturated $C_{5-10}$ aliphatic ring, or a substituted or unsubstituted $C_{5-10}$ aromatic ring, the substituent being one or more substances selected from the group consisting of hydrogen, halogen atoms, hydroxy, —OCF$_3$, —NH$_2$, —NHC$_{1-4}$ alkyl, —N(C$_{1-4}$ alkyl)$_2$, —CONH$_2$, —CONHC$_{1-4}$ alkyl, —CON(C$_{1-4}$ alkyl)$_2$, —NHCOC$_{1-4}$ alkyl, $C_{1-6}$ alkyl, $C_{1-6}$ alkoxy or $C_{3-6}$ cycloalkyl, and when two substituents are contained, the two substituents can form a ring structure together with the carbon connected thereto; and the halogen atoms are selected from the group consisting of F, Cl or Br.

The compound according to the present invention has a structure as shown in the following Formula (II):

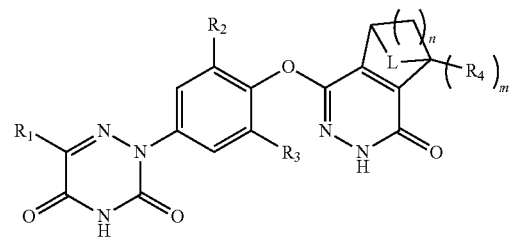

(II)

wherein, $R_1$ to $R_3$ are defined as described in the above Formula (I);

L is not present or is selected from the group consisting of —CH$_2$— and —CH$_2$CH$_2$—;

$R_4$ is selected from the group consisting of hydrogen, halogen atoms, hydroxy, —OCF$_3$, —NH$_2$, —NHC$_{1-4}$ alkyl, —N(C$_{1-4}$ alkyl)$_2$, $C_{1-6}$ alkyl, $C_{1-6}$ alkoxy or $C_{3-6}$ cycloalkyl;

n is an integer from the range 1 to 4;

m is an integer from the range 1 to 4; and when L is not present, the ring may have two or more substituents $R_4$ thereon; and the halogen atoms are selected from the group consisting of F, Cl or Br.

Preferably, in the structure as shown in Formula (II), $R_4$ is selected from the group consisting of hydrogen, halogen atoms, hydroxy, $C_{1-3}$ alkyl, $C_{1-3}$ alkoxy or $C_{3-6}$ cycloalkyl;

L is not present or is selected from the group consisting of —CH$_2$— or —CH$_2$CH$_2$—;

n is 1, 2 or 3; and m is 1 or 2.

Further preferably, in the structure as shown in Formula (II), $R_4$ is selected from the group consisting of hydrogen or $C_{1-3}$ alkyl;

L is —CH$_2$— or —CH$_2$CH$_2$—;

n is 1, 2 or 3; and m is 1 or 2.

Further preferably, in the structure as shown in Formula (II), $R_4$ is selected from the group consisting of hydrogen or $C_{1-3}$ alkyl;

L is not present;

n is 1, 2 or 3; and m is 1 or 2.

The compound according to the present invention has a structure as shown in the following Formula (III):

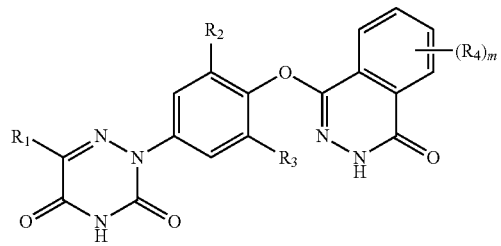

wherein, $R_1$ to $R_3$ are defined as described in the above Formula (I);

$R_4$ is selected from the group consisting of hydrogen, halogen atoms, hydroxy, —OCF$_3$, —NH$_2$, —NHC$_{1-4}$ alkyl, —N(C$_{1-4}$ alkyl)$_2$, —CONH$_2$, —CONHC$_{1-4}$ alkyl, —CON(C$_{1-4}$ alkyl)$_2$, —NHCOC$_{1-4}$ alkyl, C$_{1-6}$ alkyl, C$_{1-6}$ alkoxy or C$_{3-6}$ cycloalkyl;

m is an integer from the range 1 to 4; and the halogen atoms are selected from the group consisting of F, Cl or Br.

Preferably, in the structure as shown in Formula (III), R$_4$ is selected from the group consisting of hydrogen, halogen atoms, hydroxy, —OCF$_3$, C$_{1-6}$ alkyl, C$_{1-6}$ alkoxy or C$_{3-6}$ cycloalkyl; and m is an integer from the range 1 to 3.

Preferably, in the structure as shown in Formula (III), R$_4$ is selected from the group consisting of hydrogen, halogen atoms or C$_{1-3}$ alkyl; and m is 1 or 2.

Preferably, in the above compound having the structure of Formula (I), (II) or (III) according to the present invention, R$_1$ is selected from the group consisting of hydrogen, cyano, substituted or unsubstituted C$_{1-6}$ alkyl; further preferably, R$_1$ is selected from the group consisting of cyano or C$_{1-3}$ alkyl; and still further preferably, R$_1$ is cyano.

Preferably, in the above compound having the structure of Formula (I), (II) or (III) according to the present invention, R$_2$ and R$_3$ are each independently selected from the group consisting of F, Cl or Br, and further preferably, both R$_2$ and R$_3$ are Cl.

Preferably, the compound and pharmaceutically acceptable salt thereof according to the invention are one of the following compounds:

1

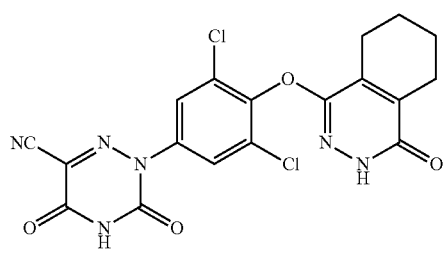

2

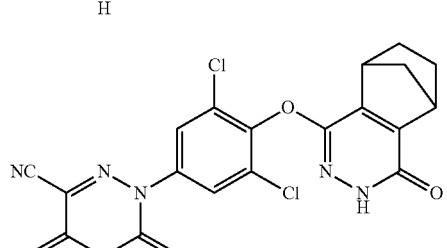

3

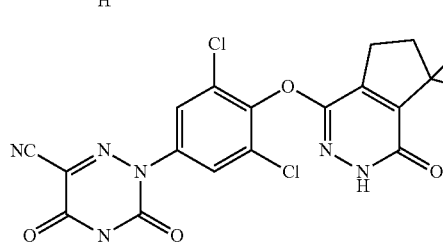

4

5

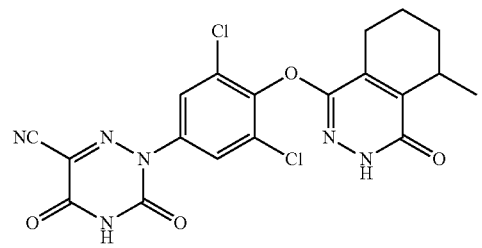

6

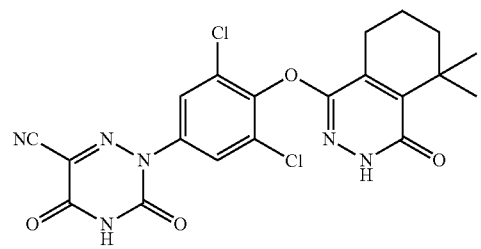

7

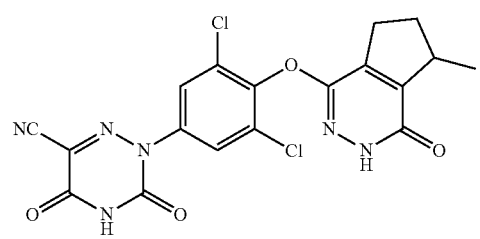

8

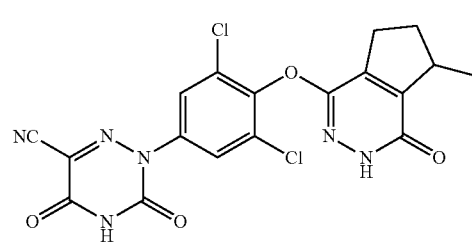

9

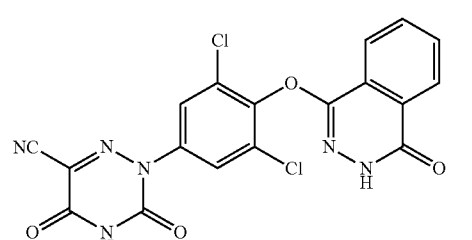

10

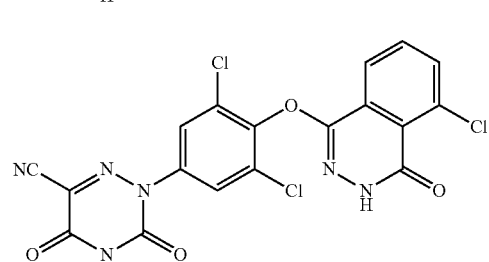

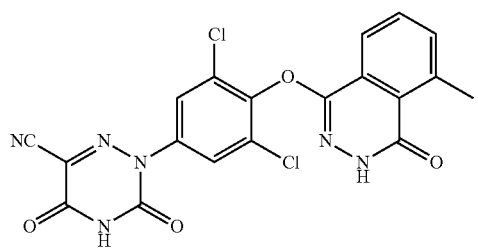
11
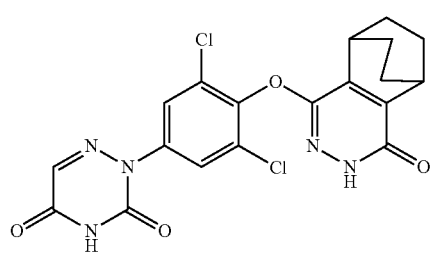
12
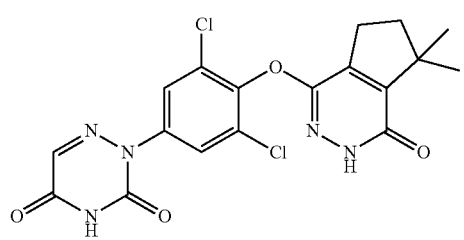
13
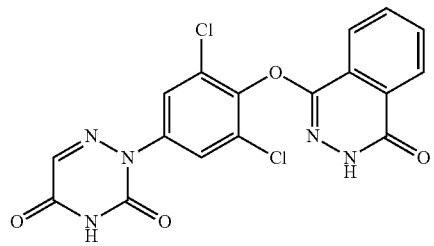
14
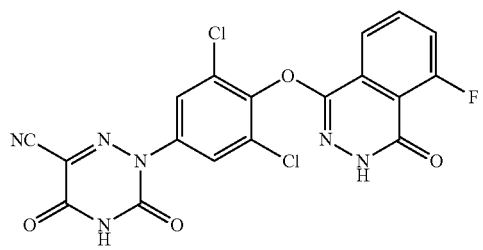
15
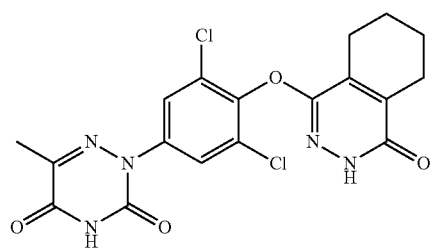
16
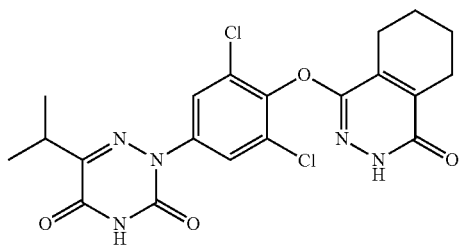
17
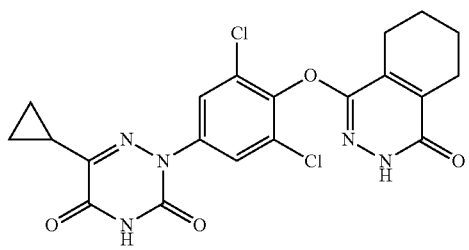
18
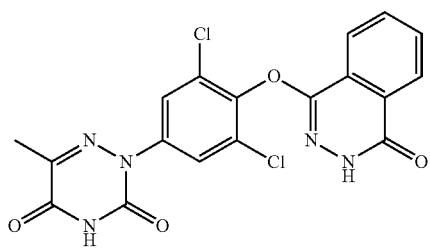
19
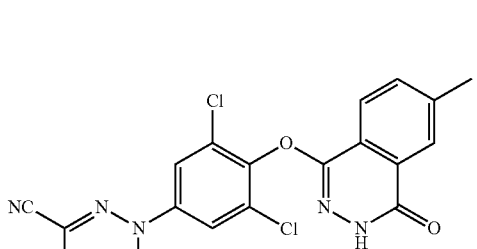
20
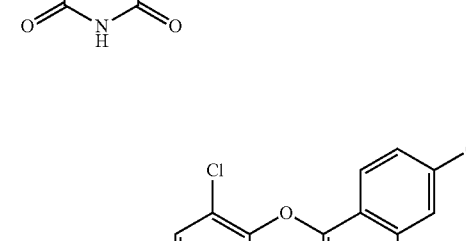
21
According to another aspect of the present invention, the present invention provides a method for preparing the compound, the preparation method comprising the following steps:

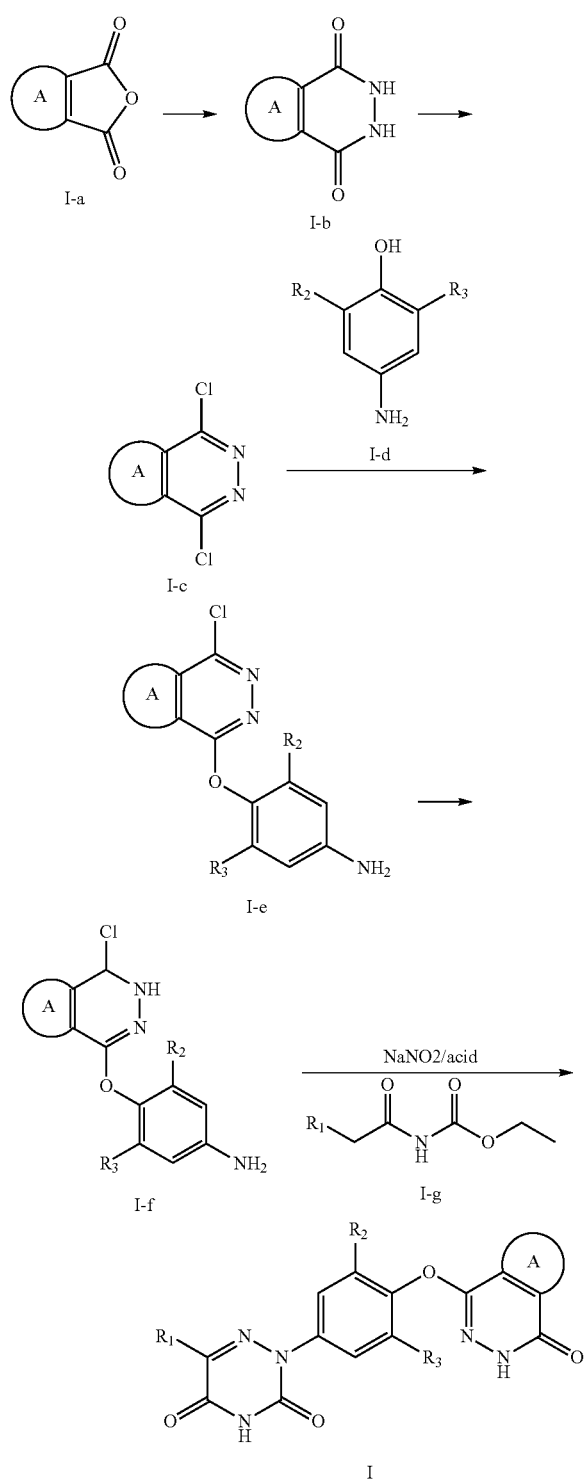

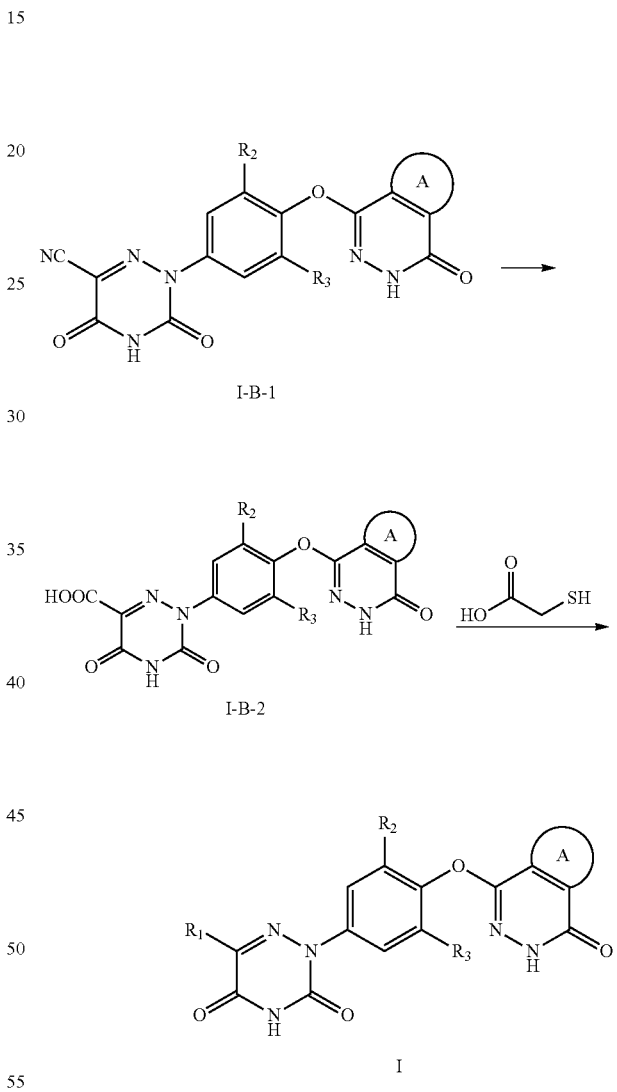

general formula I-e, where the catalyst at this condition is preferably cuprous iodide;

4) reacting the obtained compound of the general formula I-e at acidic or alkaline high temperature, to obtain a compound of the general formula I-f, and 5) reacting the obtained compound of the general formula I-f with sodium nitrite in an aqueous acidic solution, followed by the addition of a compound I-g for further reaction and ring closing at high temperature, to obtain a compound of the general formula I, where the acid is preferably hydrochloric acid under this condition.

The compound of the general formula I according to the present invention may also be prepared as follows:

1) reacting the internal anhydride compound I-a with hydrazine hydrochloride, to obtain a compound of the general formula I-b;
2) heating the obtained compound of the general formula I-b in phosphorus oxychloride, to form a compound of the general formula I-c;
3) subjecting the obtained compound of the general formula I-c and the compound I-d to coupling reaction at high temperature, to obtain a compound of the The compound of the general formula I-B-1 is subjected to high-temperature hydrolysis in an aqueous acidic solution, to obtain a compound of the general formula I-B-2, where the acid is preferably hydrochloric acid under this condition; and the obtained compound of the general formula I-B-2 is reacted in the presence of mercaptoacetic acid at a high temperature to eliminate carboxy, to obtain the compound of the general formula I.

The compound of the general formula I according to the present invention may also be prepared through the following method:

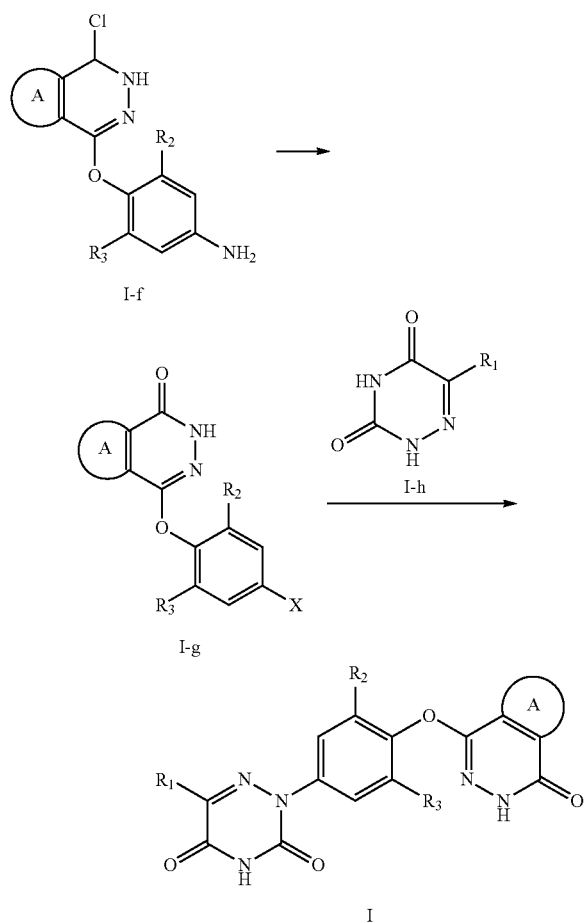

The compound of the general formula I-f is reacted with sodium nitrite under an acidic condition, to form a diazonium salt compound, followed by the addition of a halide anion, to obtain a compound of the general formula I-g; and under the catalysis of a transition metal, the obtained compound of the general formula I-g is coupled with the intermediate I-h, to obtain the compound of the general formula I.

According to another aspect of the present invention, the present invention provides use of the compound in the preparation of a therapeutic drug for a metabolism-related disease.

According to another aspect of the present invention, the present invention provides a pharmaceutical composition comprising a therapeutically effective amount of the compound according to the present invention and a pharmaceutically acceptable salt thereof as an active ingredient, and a pharmaceutically acceptable adjuvant.

Preferably, the metabolism-related disease is selected from the group consisting of obesity, hyperlipidemia, hypercholesterolemia, diabetes, and non-alcoholic steatohepatitis (NASH), steatosis of liver, atherosclerosis, hypothyroidism, and thyroid cancer; and preferably, the metabolism-related disease is selected from the group consisting of non-alcoholic steatohepatitis (NASH), hypothyroidism and thyroid cancer.

According to another aspect of the present invention, the present invention provides a method for treating a metabolism-related disease, the method comprising administering to the subject an effective amount of the compound according to the present invention or a pharmaceutical composition comprising the compound and pharmaceutically acceptable salt thereof as an active ingredient.

Preferably, according to the method for treating the metabolism-related disease, the metabolism-related disease is selected from the group consisting of: obesity, hyperlipidemia, hypercholesterolemia, diabetes, and non-alcoholic steatohepatitis (NASH), steatosis of liver, atherosclerosis, hypothyroidism, and thyroid cancer; and preferably, the metabolism-related disease is selected from the group consisting of non-alcoholic steatohepatitis (NASH), hypothyroidism and thyroid cancer.

DETAILED DESCRIPTION

The present invention is described below in detail. Prior to the description, it should be understood that, the terms used in the specification and the appended claims shall not be interpreted to be limited to the general meaning and dictionary meaning, but shall be interpreted according to the corresponding meaning and concepts in the technical aspects of the present invention on the basis of the principle that the inventor is allowed to properly define the terms for the best interpretation. Therefore, the description proposed here is only a preferred example for the purpose of illustration, and is not intended to limit the scope of the invention. Hence it should be understood that other equivalents or improvements can be obtained from it without departing from the spirit and scope of the present invention.

According to the present invention, all terms quoted herein have the same meaning as those skilled in the art that understand the invention, unless otherwise specified.

As used herein, the term "salt" refers to a compound containing cations and anions, which can be formed by protonation of a site that can accept protons and/or proton abstraction of a site that can supply protons. It is worth noting that the protonation of the site that can accept protons leads to the formation of a cationic substance, and the charge thereof is balanced by the presence of physiological anions, whereas the proton abstraction of the site that can supply protons leads to the formation of an anionic substance, and the charge thereof is balanced by the presence of physiological cations.

The term "pharmaceutically acceptable salt" refers that the salt is pharmaceutically acceptable. Examples of the pharmaceutically acceptable salt include, but are not limited to: (1) acid addition salts, formed with inorganic acid, e.g., hydrochloric acid, hydrobromic acid, sulfuric acid, nitric acid, and phosphoric acid; or formed with organic acid, e.g., glycolic acid, pyruvic acid, lactic acid, malonic acid, malic acid, maleic acid, fumaric acid, tartaric acid, citric acid, 3-(4-hydroxybenzoyl)benzoic acid, cinnamic acid, mandelic acid, methanesulfonic acid, ethanesulfonic acid, 1,2-ethanedisulfonic acid, 2-hydroxyethane sulfonic acid, benzene sulfonic acid, 4-chlorobenzenesulfonic acid, 2-naphthalenesulfonic acid, 4-paratoluenesulfonic acid, camphoric acid, dodecylsulfuric acid, gluconic acid, glutamic acid, salicylic acid, and cis-muconic acid; or (2) alkali addition salts, formed with any conjugate base of the above inorganic acids, where the conjugate base comprises a cationic component selected from the group consisting of $Na^+$, $K^+$, $Mg^{2+}$, $Ca^{2+}$, and $NH_xR_{4-x}^+$, where $NH_xR_{4-x}^+$ (R is $C_{1-4}$ alkyl, and the subscript x is an integer selected from the group consisting of 0, 1, 2, 3 or 4) represents the cation in the quaternary ammonium salt. It should be understood that, all pharmaceutically acceptable salts involved include the solvent addition form (solvate) or crystal form (polymorphic substance) as defined herein for the same acid addition salt.

The term "$C_{1-M}$ alkyl" refers to alkyl comprising 1 to M carbon atoms, e.g., where M is an integer having the following numerical value: 2, 3, 4, 5, 6, 7, 8, 9, 10, 11, 12, 13, 14, 15, 16, 17, 18, 19, 20, 21, 22, 23, 24, 25, 26, 27, 28, 29 or 30. For example, the term "$C_{1-6}$ alkyl" refers to alkyl containing 1 to 6 carbon atoms. Examples of alkyl include, but are not limited to lower alkyl, including methyl, ethyl, propyl, i-propyl, n-butyl, i-butyl, t-butyl or amyl, i-amyl, neopentyl, hexyl, heptyl and octyl.

The term "aromatic group" refers to an aromatic system, which may be a monocyclic ring, or a poly-aromatic ring originally fused or joined together such that at least a part of the fused or joined rings form a conjugated aromatic system. Aryl groups include, but are not limited to: phenyl, naphthyl and tetralyl. Aryl may be optionally substituted by, e.g., 1 to 4 aryl groups or heterocyclic rings substituted by a group selected from the group consisting of: halogen, —CN, —OH, —NO$_2$, amino, alkyl, cycloalkyl, alkenyl, alkynyl, alkoxy, aryloxy, substituted alkoxy, alkylcarbonyl, alkylcarboxy, alkylamino, or arylthio.

The term "substitute" refers to that the reference group can be substituted by one or a plurality of additional groups, where the additional groups are separately and independently selected from the group consisting of alkyl, cycloalkyl, aryl, heteroaryl, heteroalicyclic hydrocarbon, hydroxy, alkoxy, alkylthiol, arylthio, alkylsulfinyl, arylsulfinyl, alkylsulfonyl, arylsulfonyl, cyano, halo, carbonyl, thiocarbonyl, nitro, haloalkyl, fluoroalkyl and amino, including monosubstituted and disubstituted amino groups and derivatives protected by them.

The compound represented by Formula (I) or pharmaceutically acceptable salt thereof provided by the present invention, and pharmaceutical compositions containing the compound may be in various forms, such as tablets, capsules, powders, syrups, solutions, suspensions and aerosols, etc., and may exist in a suitable solid or liquid carrier or diluent, and in a disinfector suitable for injection or infusion.

Various dosage forms of the pharmaceutical composition of the present invention can be prepared according to preparation methods conventional in the field of pharmacy. For example, the unit dose of the preparation formula contains 0.05 to 200 mg of the compound of Formula (I) or pharmaceutically acceptable salt thereof, and preferably, the unit dose of the preparation formula contains 0.1 to 100 mg of the compound of Formula (I).

The compound represented by the general formula (I) or pharmaceutical compositions provided by the present invention can be used clinically in mammals, including humans and animals, through dosage routes such as oral, nasal, transdermal, transpulmonary or gastro-intestinal tract routes. Oral administration is the most preferred. The most preferred daily dose is 0.01 to 200 mg/kg of weight per single administration, or 0.01 to 100 mg/kg of weight per separate administration. Regardless of the administration method, the best dose for an individual should be decided on the basis of the specific treatment. Usually administration starts at a small dose and increases gradually until the most suitable dose is found.

In the present invention, the term "effective amount" may refer to the effective amount for the dose and time period required to achieve the expected effect. This effective dose may vary differently due to certain factors, such as the disease type, symptoms of the disease at the time of treatment; the structure of the specific target organ to be administered; the individual height and weight of the patient, or the severity of the disease or symptom. Those of ordinary skill in the art can determine, by experience, the effective amount of a specific compound without conducting unneeded experiments.

A typical formula is prepared by mixing the compound represented by the general formula (I) of the invention, and a carrier, a diluent or an excipient. Suitable carriers, diluents or excipients are well known to those of skill in the art, including substances such as carbohydrates, waxes, water-soluble and/or expandable polymers, hydrophilic or hydrophobic substances, gelatin, oil, solvents, and water.

The specific carrier, diluent or excipient to be used shall be decided according to the usage and purpose of the compound of the present invention. Generally, the solvent is selected on the basis of the solvents which can be safely and effectively dosed to mammals according to those skilled in the art. In general, safe solvents are non-toxic aqueous solvents such as water and other non-toxic solvents that are soluble in or miscible with water. Suitable aqueous solvents include one or a plurality of water, ethanol, propylene glycol, polyethylene glycol (such as PEG400, and PEG300) and the like. The formula may also include one or a plurality of buffers, stabilizers, surfactants, wetting agents, lubricants, emulsifiers, suspending agents, preservatives, antioxidants, light-screening agents, flow aids, processing aids, colorants, sweeteners, fragrances, flavoring agents or other known additives, to enable the drug to be manufactured or used in an acceptable form.

When the compound of Formula (I) of the present invention is used in combination with at least one other drug, the two or more drugs can be used separately or in combination, preferably in the form of a pharmaceutical composition. The compound of Formula (I) or the pharmaceutical composition according to the present invention can be dosed to the subject separately or together, in any known oral, intravenous, rectal, vaginal, transdermal, other topical or systemic dosage forms.

These pharmaceutical compositions may also contain one or a plurality of buffers, stabilizers, surfactants, wetting agents, lubricants, emulsifiers, suspending agents, preservatives, antioxidants, light-screening agents, flow aids, processing aids, colorants, sweeteners, fragrances, flavoring agents, or other known additives, to enable the pharmaceutical compositions to be manufactured or used in an acceptable form.

The oral dosage route is preferred for the drug of the present invention. The solid dosage form for oral dosage may include capsules, tablets, powders or particle formulations. In the solid dosage form, the compound or pharmaceutical composition according to the present invention is mixed with at least one inert excipient, diluent, or carrier. Suitable excipients, diluents, or carriers include substances such as sodium citrate or dicalcium phosphate, or starch, lactose, sucrose, mannitol, silicic acid, and the like; adhesives such as carboxymethyl cellulose, alginate, gelatin, polyvinyl pyrrolidone, sucrose, and Arabia gum; wetting agents such as glycerol; disintegrating agents such as agar, calcium carbonate, potato or cassava starch, alginic acid, specific complex silicate, and sodium carbonate; solution blockers such as paraffin; absorption promoters such as quaternary ammonium compounds; adsorbents such as kaolin and bentonite; and lubricants such as talc, calcium stearate, magnesium stearate, solid polyethylene glycol, and sodium lauryl sulfate. In the case of capsules and tablets, the dosage form may also include buffers. Similar types of solid compositions may also be used as fillers in soft and hard filled gelatin capsules, which use lactose and high molecular weight polyethylene glycol as excipients.

Liquid dosage forms for oral administration include pharmaceutically acceptable emulsions, solutions, suspensions, and syrups and elixirs. In addition to the compound or the pharmaceutical composition thereof according to the present invention, the liquid dosage form may contain inert diluents commonly used in the art, such as water or other solvents; solubilizers and emulsifiers such as ethanol, isopropyl alcohol, ethyl carbonate, ethyl acetate, benzyl alcohol, benzyl benzoate, propylene glycol, 1,3-butanediol, dimethylformamide; oils (e.g., cotton seed oil, peanut oil, corn germ oil, olive oil, castor oil, and sesame oil); glycerol; tetrahydrofurfuryl alcohol; fatty acid esters of polyethylene glycol and sorbitan; or mixtures of several of these substances, etc.

In addition to these inert diluents, the composition may also include an excipient, such as one or a plurality of wetting agents, emulsifiers, suspending agents, sweeteners, flavoring agents, and fragrances.

In terms of the suspension, in addition to the compound represented by the general formula (I) or pharmaceutically acceptable salt thereof or the pharmaceutical composition comprising the same according to the present invention, the suspension may further contain carriers such as suspending agents, for example, ethoxylated isostearol, polyoxyethylene sorbitol, sorbitan ester, microcrystalline cellulose, aluminum metahydroxide, bentonite, agar and tragacanth gum, or mixtures of several of these substances, etc.

The compound represented by the general formula (I) or a pharmaceutically acceptable salt thereof or the pharmaceutical composition comprising the same according to the present invention may be dosed using other topical dosage forms, including ointments, powders, sprays and inhalants. This drug can be mixed under sterile conditions with pharmaceutically acceptable excipients, diluents or carriers and any preservatives, buffers or propellants required. Ophthalmic formulae, ophthalmic ointments, powders, and solutions are also intended to be encompassed in the scope of the present invention.

In addition, the present disclosure further encompasses kits (e.g., pharmaceutical packages). The kit provided may comprise the pharmaceutical composition or the compound described herein and containers (e.g., drug bottles, ampoules, bottles, syringes and/or subpackages or other suitable containers). In some embodiments, the kit provided may optionally further include a second container comprising a pharmaceutical excipient for diluting or suspending the pharmaceutical composition or the compound described herein. In some embodiments, the pharmaceutical composition or the compound described herein provided in the first and the second containers are combined to form a unit dosage form.

In some embodiments, the kit described herein further includes instructions of use of the compound or the pharmaceutical composition comprised in the kit. The kit described herein may also include information required by regulatory agencies such as the US Food and Drug Administration (FDA). In some embodiments, the information included in the kit is formula information. In some embodiments, the kit and the instructions are provided for the treatment of a proliferative disease in subjects in need thereof and/or prevention of a proliferative disease of subjects in need thereof. The kit described herein may comprise one or a plurality of additional pharmaceutical preparations as separate compositions.

The present invention will be further described below in detail in combination with particular embodiments, but the present invention is not limited to the following embodiments which serve the purpose of better explaining specific embodiments of the present invention and should not be interpreted as limiting the scope of the invention in any way. The conditions not noted in the embodiments are conventional conditions. Unless stated particularly, the reagents and apparatuses used in the following embodiments are all commercially available products.

The structures of the compounds in the following embodiments are determined by nuclear magnetic resonance (NMR) or/and mass spectrometry (MS). The NMR displacement (δ) is given in the unit of 10-6 (ppm). For the determination by NMR, a Bruker AVANCE-400 nuclear magnetic instrument is used. Solvents are deuterated dimethyl sulfoxide (DMSO-d6), deuterated chloroform (CDCl3) and deuterated methanol (CD3OD), and the internal standard is tetramethylsilane (TMS).

For determination by MS, a FINNIGAN LCQAd (ESI) mass spectrometer (manufacturer: Thermo, model: Finnigan LCQ advance max) is used.

Yantai Huanghai HSGF254 or Qingdao GF254 silica gel plates are used as the silica gel plates for the thin-layer chromatography. The specification of the silica gel plate for the thin-layer chromatography (TLC) is 0.15 mm to 0.2 mm, and the specification for that in the thin-layer chromatography for separation and purification of products is 0.4 mm to 0.5 mm.

Column chromatography generally uses Yantai Huanghai silica gel 200-300 mesh silica gel as the carrier.

When no special description in the embodiments exists, the reaction temperature is room temperature, i.e., 20° C. to 30° C.

The thin-layer chromatography (TLC) is employed to detect the reaction process in the embodiments. The developer system used and the eluent system of column chromatography employed for purifying the compound include: A: a dichloromethane and methanol system; B: a n-hexane and ethyl acetate system; C: a petroleum ether and ethyl acetate system; D: an acetone and petroleum ether system, where the ratio by volume of the solvents is adjusted according to different polarities of the compounds.

Embodiment 1: Preparation of 2-(3,5-dichloro-4-((4-oxo-3,4,5,6,7,8-hexahydrophthalazin-1-yl)oxy)phenyl)-3,5-dioxo-2,3,4,5-tetrahydro-1,2,4-triazine-6-nitrile

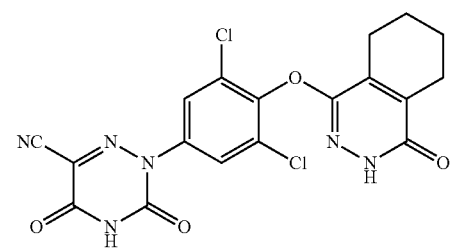

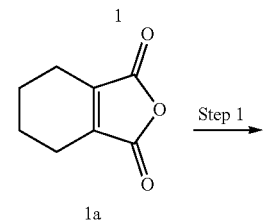

Step 1

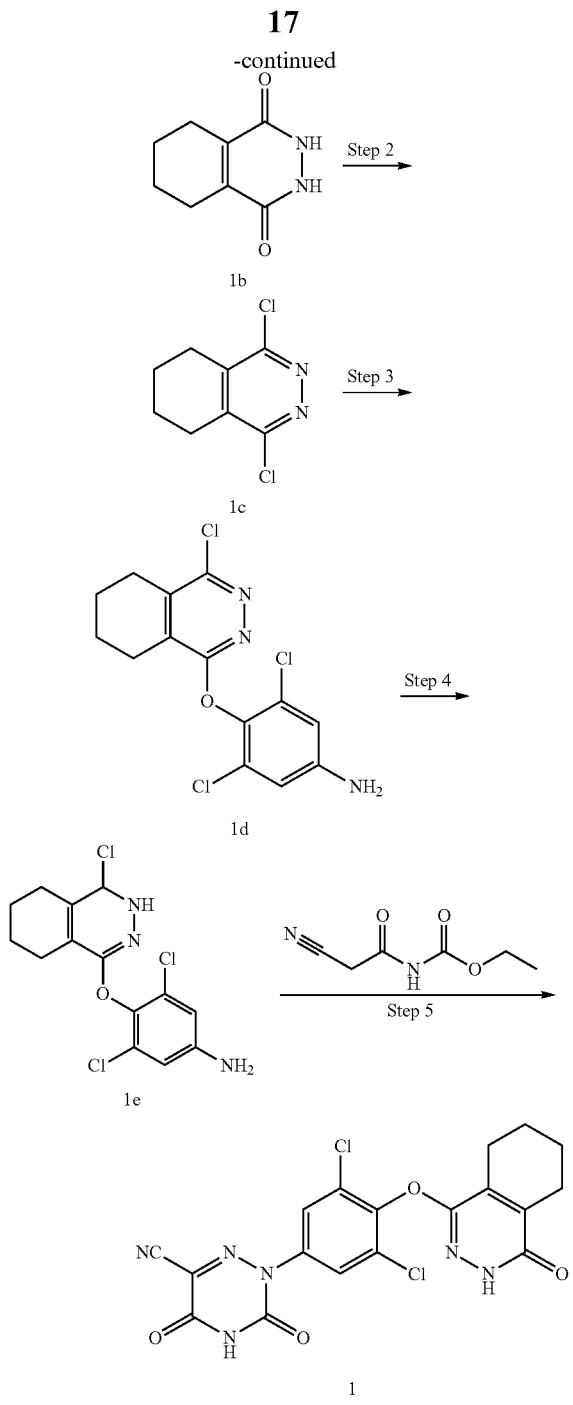

$^{1}$H NMR (400 MHz, DMSO-$d_6$): 11.26 (s, 2H), 2.36 (s, 4H), 1.65 (s, 4H).

Step 2: Preparation of 1,4-dichloro-5,6,7,8-tetrahydrophthalazine (Compound 1c)

The compound 1b (1 g, 6.02 mmol) was dissolved into phosphorus oxychloride (8 ml). The air in the system was replaced 3 times with nitrogen gas. The system was warmed up to a temperature of 110° C. and stirred for 3 h. The reaction was stopped and then naturally cooled. The reaction solution was slowly dripped into ice water. The mixture was adjusted to pH 10 with a 1N sodium hydroxide aqueous solution and extracted 3 times with ethyl acetate. Organic phases were combined, and the organic phase was washed with saturated brine and concentrated to dry, to obtain a compound 1c (1.1 g). The product was directly used in the next reaction.

Step 3: Preparation of 3,5-dichloro-4-((4-chloro-5,6,7,8-tetrahydrophthalazin-1-yl)oxy)aniline (Compound 1d)

Dimethyl sulfoxide (8 ml) was added into the mixture of the compound 1c (1.0 g, 5.0 mmol), 2,6-dichloro-4-aminophenol (0.93 g, 6 mmol), potassium carbonate (2.76 g, 20 mmol), and CuI (0.57 g, 3 mmol). The air in the system was replaced 3 times with nitrogen gas. The system was warmed up to a temperature of 100° C. and stirred for 3 h. After the reaction was stopped, it was cooled. The solid in the reaction solution was filtered out first, and the filter residue was washed repeatedly with ethyl acetate. 80 ml of water was added into the filtrate, and then the aqueous phase was extracted with ethyl acetate reaction. The organic phases were combined and washed with saturated brine. A compound 1d (450 mg) was obtained by column chromatography after filtration and solvent concentration.

Step 4: Preparation of 4-(4-amino-2,6-dichlorophenoxy)-5,6,7,8-tetrahydrophthalazin-1(2H)-one (Compound 1e)

The compound 1d (100 mg, 0.3 mmol) was dissolved into acetic acid (4 ml), and sodium acetate (200 mg, 2.5 mmol) was added therein. The mixture was heated to a temperature of 120° C. and stirred for 12 h. After the reaction was stopped, the solvent was removed under reduced pressure. 10 ml of water was added therein, and then a 1N sodium hydroxide aqueous solution was added to adjust the pH to 8. Then extraction was carried out with ethyl acetate (10 ml×3), and organic phases were combined. The organic phase was washed with a saturated aqueous sodium bicarbonate solution and saturated brine respectively, and concentrated under reduced pressure to obtain a gray solid. 10 ml of methanol and 10 ml of a 1N sodium hydroxide aqueous solution were added into the solid obtained, and the mixture was heated to a temperature of 120° C. and stirred for 12 h. After the reaction was stopped, methanol was concentrated under reduced pressure. The remaining aqueous phase was extracted 3 times with ethyl acetate repeatedly, and organic phases were combined. After the solvent was concentrated under reduced pressure, compound 1e (80 mg) was obtained by separation and purification through thin-layer chromatography.

Step 1: Preparation of 2,3,5,6,7,8-hexahydrophthalazin-1,4-dione (Compound 1b)

Sodium acetate (3.69 g, 45 mmol) and hydrazine hydrochloride (3.08 g, 45 mmol) were successively added into a solution of a compound 3,4,5,6-tetrahydrophthalic anhydride 1a (4.56 g, 30 mmol) in acetic acid (50 ml) and water (100 ml). After the addition, the mixture was warmed up to a temperature of 100° C. and stirred for 3 h. The reaction was stopped and naturally cooled to room temperature. A solid was precipitated and filtered out to obtain a compound 1b (4.2 g), and the product was directly used in the next reaction.

Step 5: Preparation of 2-(3,5-dichloro-4-((4-oxo-3,4,5,6,7,8-Hexahydrophthalazin-1-yl)oxy)phenyl)-3,5-dioxo-2,3,4,5-tetrahydro-1,2,4-triazine-6-nitrile (Compound 1)

Sodium nitrite (16 mg) was dissolved into water (0.5 mL). Under ice bath conditions, this solution was slowly added dropwise into a mixture of a compound 1e (60 mg, 0.185 mmol), water (2.5 mL) and a saturated aqueous hydrochloric acid solution (1.25 mL), and stirred for 0.5 h with the ice bath conditions maintained, until the solution became clear. At this temperature, a mixed solution of N-cyanoacetylurethane (32 mg) in water (4.2 ml) and pyridine (1.3 ml) was additionally added dropwise, and stirred overnight after the dropwise addition. After the reaction was stopped, a yellow solid was filtered out, and washed with water and petroleum ether. Acetic acid (5 ml) and sodium acetate (160 mg, 2 mmol) were added into the solid obtained. The mixture was heated to a temperature of 120° C. and stirred for 6 h, then cooled to room temperature. 100 ml of water was added therein to precipitate a light yellow solid. After separation and purification through thin-layer chromatography (DCM:MeOH=8:1), compound 1 (12.0 mg) was obtained.

$^1$H NMR (400 MHz, DMSO-d$_6$) δ 12.03 (s, 1H), 7.75 (s, 2H), 2.68-2.63 (m, 2H), 2.45-2.39 (m, 2H), 1.80-1.67 (m, 4H).

MS m/z (ESI): 447.4 [M+1].

Embodiment 2: Preparation of 2-(3,5-dichloro-4-((4-oxo-3,4,5,6,7,8-hexahydro-5,8-ethanophthalazin-1-yl)oxy)phenyl)-3,5-dioxo-2,3,4,5-tetrahydro-1,2,4-triazine-6-nitrile (Compound 2b)

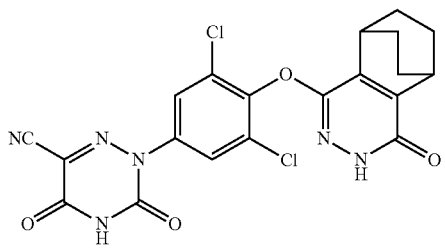

2

The synthetic route of Embodiment 1 was employed, except that the raw material 3,4,5,6-tetrahydrophthalic anhydride 1a in Step 1 was replaced with bicyclo[2.2.2]oct-2-ene-2,3-dicarboxylic anhydride, to produce the title product 2-(3,5-dichloro-4-((4-oxo-3,4,5,6,7,8-hexahydro-5,8-ethanophthalazin-1-yl)oxy)phenyl)-3,5-dioxo-2,3,4,5-tetrahydro-1,2,4-triazine-6-nitrile (compound 2).

$^1$H NMR (400 MHz, DMSO-d$_6$): 12.13 (s, 1H), 7.77 (s, 2H), 1.88-1.73 (m, 4H), 1.39-1.17 (m, 6H).

MS m/z (ESI): 473.2 [M+1].

Embodiment 3: Preparation of 2-(3,5-dichloro-4-((4-oxo-3,4,5,6,7,8-hexahydro-5,8-methanophthalazin-1-yl)oxy)phenyl)-3,5-dioxo-2,3,4,5-tetrahydro-1,2,4-triazine-6-nitrile (Compound 3)

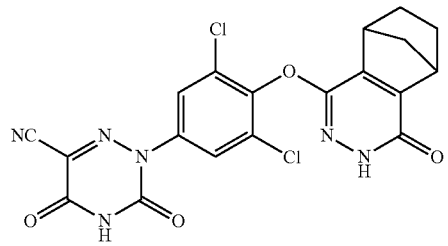

3

Step 1: Preparation of dimethyl-bicyclo[2.2.1]hepta-2,5-diene-2,3-dicarboxylate

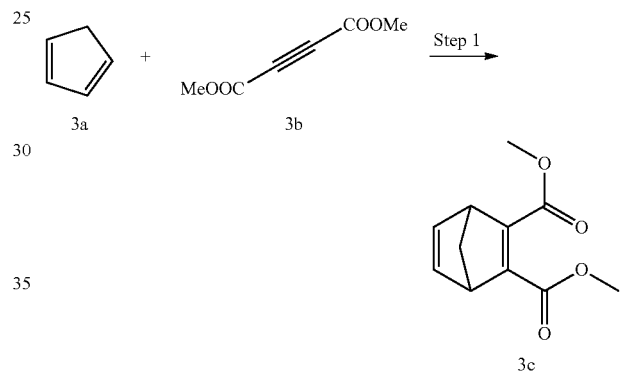

Dimethyl acetylenedicarboxylate (compound 3b) (2.75 ml, 22.3 mmol) was slowly dripped into cyclopentadiene (compound 3a) (1.475 g, 22.3 mmol), and stirred for 2 h at room temperature after the addition. The reaction was stopped, and an oily product 3c (4.0 g) was obtained. The crude product was directly used in the next reaction without purification.

Step 2: Preparation of dimethyl-bicyclo[2.2.1]hepta-2-ene-2,3-dicarboxylate

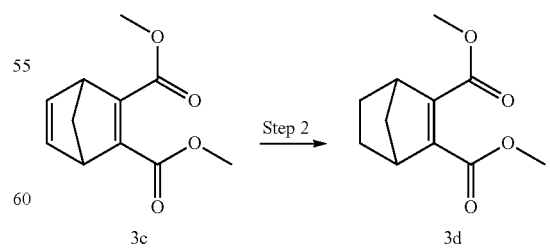

The compound 3c (1.0 g, 4.8 mmol), palladium carbon (0.05 g) and 15 ml of acetone were placed into a reaction flask, and replacement was performed 3 times under a hydrogen balloon. The system was stirred for 1 h at room temperature. Filtration was carried out, and the solvent was concentrated to dry under reduced pressure, to obtain a light green liquid product 3d (0.9 g).

Step 3: Preparation of bicyclo[2.2.1]hept-2-ene-2,3-diacid

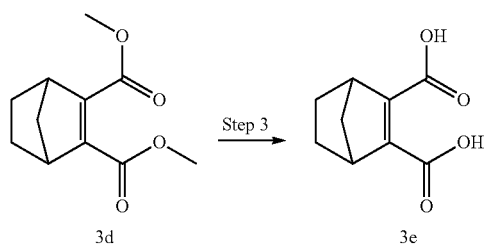

Tetrahydrofuran (20 ml) and water (20 ml) were added into a mixture of the compound 3d (3.0 g, 14.3 mmol) and lithium hydroxide monohydrate (1.54 g, 35.8 mmol), and stirred for 2 h at room temperature. The solution was adjusted to pH 1 with 2N dilute hydrochloric acid, extracted 3 times with ethyl acetate, dried over anhydrous sodium sulfate, filtered, and concentrated under reduced pressure to obtain a white solid compound 3e (2.0 g).

Step 4: Preparation of 4,5,6,7-tetrahydro-4,7-methanoisophenylfuran 1,3-dione

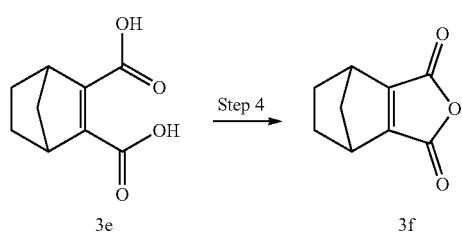 [SMILES: O=C(O)C1=C(C(=O)O)C2CCC1C2 ; O=C1OC(=O)C2=C1C1CCC2C1]

Acetic anhydride (10 mL) was added into the compound 3e (200 mg, 1.1 mmol). The mixture was heated to a temperature of 100° C. and stirred for 2 h. The solvent was removed by concentration under reduced pressure, to obtain a crude product of a solid compound 3f (200 mg).

Step 5: Preparation of 2-(3,5-dichloro-4-((4-oxo-3,4,5,6,7,8-hexahydro-5,8-methanophthalazin-1-yl)oxo)phenyl)-3,5-dioxo-2,3,4,5-tetrahydro-1,2,4-triazine-6-nitrile The synthetic route of Embodiment 1 was employed, except that the raw material 4,5,6,7-tetrahydroisobenzofuran-1,3-dione (compound 1a) in Step 1 was replaced with 4,5,6,7-tetrahydro-4,7-methanoisophenylfuran 1,3-dione (compound 3f), to produce the title product 2-(3,5-dichloro-4-((4-oxo-3,4,5,6,7,8-hexahydro-5,8-methanophthalazin-1-yl)oxo)phenyl)-3,5-dioxo-2,3,4,5-tetrahydro-1,2,4-triazine-6-nitrile (compound 3).
$^1$H NMR (400 MHz, DMSO-$d_6$) δ 12.08 (s, 1H), 7.77 (s, 2H), 2.75-2.65 (m, 2H), 1.80-1.72 (m, 4H), 1.55-1.50 (m, 2H).
MS m/z (ESI): 459.0 [M+1].

Embodiment 4: Preparation of 2-(3,5-dichloro-4-((7,7-dimethyl-1-oxo-2,5,6,7-tetrahydro-1H-cyclopenta[d]pyridazin-4-yl)oxy)phenyl)-3,5-dioxo-2,3,4,5-tetrahydro-1,2,4-triazine-6-carbonitrile (Compound 4)

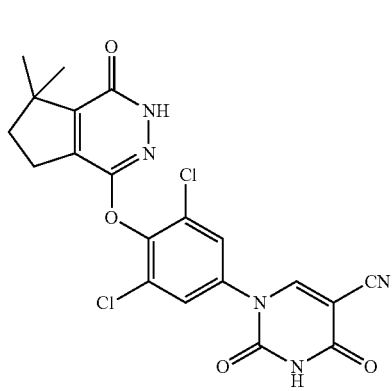

Step 1: Preparation of methyl 3,3-dimethyl-2-oxocyclopentyl-1-carboxylate

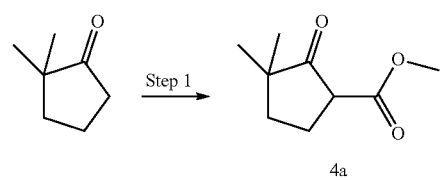

NAH (480 mg, 12 mmol) was added into a solution of a compound 2,2-dimethylcyclopentane-1-one (1.12 g, 10 mmol) and MeOH (0.5 ml) in DMC (11 ml). The mixture was heated to a temperature of 82° C., stirred for 3 h, and cooled. Methanol (0.5 ml) and acetic acid (1 ml) were successively added into the system, then the system was poured into ice water, extracted with dichloromethane, dried, and subjected to removal of the solvent under reduced pressure, to obtain a colorless oily compound 4a (1.7 g) directly used in the next step.

Step 2: Preparation of methyl 3,3-dimethyl-2-(((trifluoromethyl)sulfo)oxo)cyclopent-1-ene-1-carboxylate

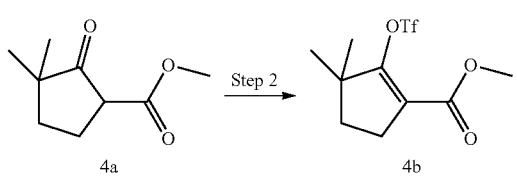

At −60° C., trifluoroacetic anhydride (2 ml, 12 mmol) added dropwise into a solution of the compound 4a (1.7 g, 10 mmol) and diisopropylethylamine (8.2 ml, 50 mmol) in dichloromethane (17 ml). After the addition, the mixture was slowly warmed up to room temperature and stirred for 16 h. 50 ml of water was added therein, and the mixture was extracted with ethyl acetate, subjected to removal of the solvent under reduced pressure, and purified through column chromatography (PE:EA=50:1), to obtain a colorless oily compound 4b (1.8 g).

Step 3: Preparation of 2-(methoxycarbonyl)-5,5-dimethylcyclopent-1-ene-1-carboxylic acid

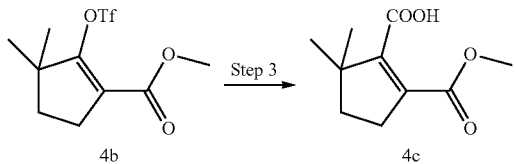

Under the atmosphere of a nitrogen gas balloon, DMF (25 ml) was added into a mixture of 4b (1.8 g, 5.96 mmol), diisopropylethylamine (1.97 ml, 11.92 mmol), acetic anhydride (1.13 ml, 11.92 mmol), sodium formate (1.22 g, 5.96 mmol), palladium diacetate (66.9 mg, 0.30 mmol), and lithium chloride (758 mg, 17.88 mmol). The system was stirred for 16 h at room temperature after the addition, and 300 ml of ethyl acetate was added into the system. The system was washed with water and saturated brine once each. The solvent was removed under reduced pressure, to obtain a colorless oil 4c (1.2 g).

Step 4: Preparation of 3,3-dimethylcyclopent-1-ene-1,2-dicarboxylic acid

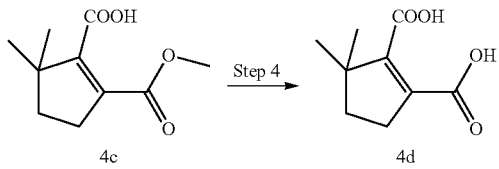

Methanol (6 ml) and water (6 ml) were added into a mixture of 4c (1.2 g, 6 mmol) and lithium hydroxide monohydrate (756 mg, 18 mmol), and stirred for 3 h at room temperature. Methanol was removed under reduced pressure, then the solution was adjusted to pH 1 with concentrated hydrochloric acid and extracted with ethyl acetate, and the solvent was removed under reduced pressure, to obtain a white solid compound 4d (1.0 g).

Step 5: Preparation of 4,4-dimethyl-5,6-dihydro-1H-cyclopentyl[c]furan-1,3(4H)-dione

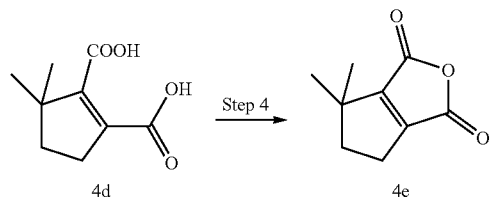

Acetic anhydride (10 ml) was added into the compound 4d (1.0 g, 5.43 mmol). The mixture was warmed up to a temperature of 100° C., stirred for 3 h, and cooled. Superfluous acetic anhydride was removed under reduced pressure, to obtain a light brown liquid compound 4e (875 mg), which was directly used in the next synthesis.

Step 6: Preparation of 2-(3,5-dichloro-4-((7,7-dimethyl-1-oxo-2,5,6,7-tetrahydro-1H-cyclopenta[d]pyridazin-4-yl)oxy)phenyl)-3,5-dioxo-2,3,4,5-tetrahydro-1,2,4-triazine-6-carbonitrile The synthetic route of Embodiment 1 was employed, except that the raw material 3,4,5,6-tetrahydrophthalic anhydride (compound 1a) in Step 1 was replaced with 4,4-dimethyl-5,6-dihydro-1H-cyclopentyl[c]furan-1,3(4H)-dione (compound 4e), to produce the title product 2-(3,5-dichloro-4-((7,7-dimethyl-1-oxo-2,5,6,7-tetrahydro-1H-cyclopenta[d]pyridazin-4-yl)oxy)phenyl)-3,5-dioxo-2,3,4,5-tetrahydro-1,2,4-triazine-6-carbonitrile (compound 4). [0103]$^1$H NMR (400 MHz, DMSO-$d_6$) δ 12.09 (s, 1H), 7.79 (s, 2H), 2.97-2.93 (m, 2H), 2.01-1.98 (m, 2H), 1.34-1.20 (m, 6H).

MS m/z (ESI): 460.9 [M+1].

Embodiment 5: Preparation of 2-(3,5-dichloro-4-((5-methyl-4-oxo-3,4,5,6,7,8-hexahydrophthalazin-1-yl)oxy)phenyl)-3,5-dioxo-2,3,4,5-tetrahydro-1,2,4-triazine-6-carbonitrile (Compound 5)

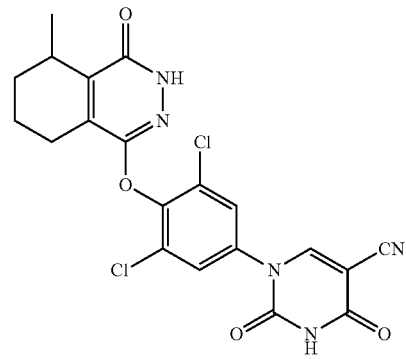

Step 1: Preparation of methyl 3-methyl-2-oxocyclohexane-1-carboxylate 5b

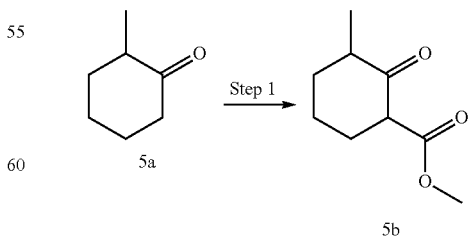

NaH (60% content, 1.92 g, 48 mmol) was added into a solution of 2-methylcyclohexanone (compound 5a) (4.48 g, 40 mmol) in dichloromethane (50 ml). The mixture was heated to reflux, stirred for 3 h, and cooled. The mixture was roughly quenched with methanol (0.5 ml) and acetic acid (1 ml). The reaction system was added into an ice bath and extracted with dichloromethane. The solvent was removed under reduced pressure, and an oil (compound 5b) (5.6 g) was obtained by purification through column chromatography.

Step 2: Preparation of methyl 3-methyl-2-(((trifluoromethyl)sulfo)oxo)cyclohexyl-1-ene-1-carboxylate

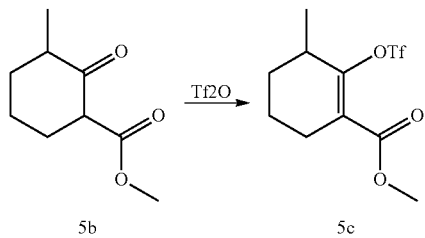 [SMILES: "Tf2O" ; COC(=O)C1CCCC(C)C1=O ; COC(=O)C1=C(OS(=O)(=O)C(F)(F)F)C(C)CCC1]

Under ice bath conditions, NaH (60% content, 600 mg, 25 mmol) was added into compound 5b (0.85 g, 5 mmol) in ethyl ether (20 ml), and stirred for 0.5 h. Then trifluoromethanesulfonic anhydride (2.8 g, 10 mmol) was added dropwise into the system and further stirred for 1 h at a temperature of 0° C. The system was quenched with H$_2$O (50 ml) added, adjusted to pH 1 with 1N HCl added, and extracted with dichloromethane. The solvent was removed under reduced pressure, and a colorless oily compound 5c (1.04 g) was obtained by purification through column chromatography (PE:EA=20:1).

Step 3: Preparation of 2-(methoxycarbonyl)-6-methylcyclohexyl-1-ene-1-carboxylic acid

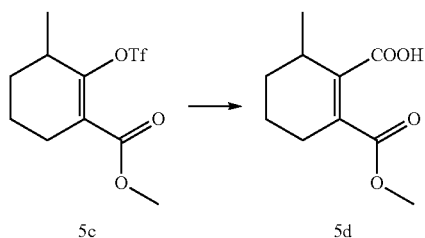 [SMILES: COC(=O)C1=C(OS(=O)(=O)C(F)(F)F)C(C)CCC1 ; COC(=O)C1=C(C(=O)O)C(C)CCC1]

Under a nitrogen atmosphere, diisopropylethylamine (0.714 g, 7.00 mmol) and acetic anhydride (0.903 g, 7.00 mmol) were successively added dropwise into a solution of the compound 5c (0.714 g, 10.5 mmol) and sodium formate (0.714 g, 10.50 mmol) in N,N-dimethyl formamide (15 ml), and stirred for 1 h at room temperature. Then palladium acetate (40 mg, 0.18 mmol) and lithium chloride (445 mg, 10.50 mmol) were added, and the system was stirred overnight at room temperature. Ethyl acetate (30 ml) was added therein, and the mixture was washed with water. The solvent was removed under reduced pressure, to obtain a light yellow oily compound 5d (590 mg).

Step 4: Preparation of 3-methylcyclohexyl-1-ene-1,2-diacid 5e

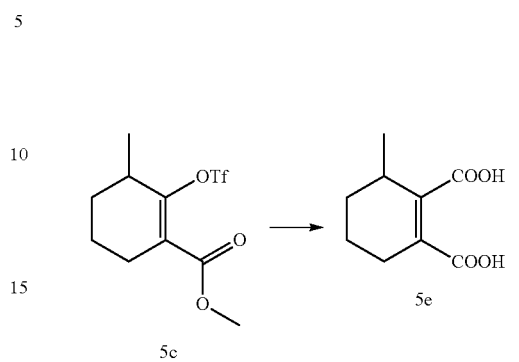

Lithium hydroxide monohydrate (0.375 g, 8.94 mmol) was added into a solution of the compound 5d (0.590 g, 2.98 mmol) in methanol (3 ml) and water (3 ml), and stirred for 3 h at room temperature. Then methanol was removed under reduced pressure. The system was adjusted to pH 1 with a 1N aqueous hydrochloric acid solution added, and extracted 3 times with ethyl acetate. The organic phases were combined, and concentrated under reduced pressure to remove the solvent, to obtain an oily compound 5e (0.550 g).

Step 5: Preparation of 4-methyl-4,5,6,7-tetrahydroisophenylfuran-1,3-dione 5f

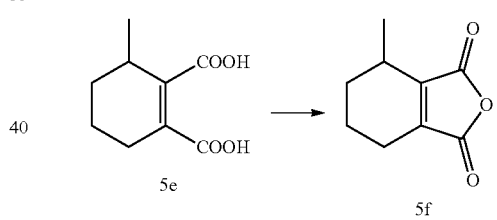

Acetic anhydride (6 ml) was added into the compound 5e (0.550 g, 2.99 mmol). The mixture was warmed up to a temperature of 100° C., and stirred for 2 h. The system was cooled, and the solvent was removed under reduced pressure, to obtain a brown oily compound 5f (0.34 g) directly used in the next synthesis.

Step 6: Preparation of 2-(3,5-dichloro-4-((5-methyl-4-oxo-3,4,5,6,7,8-hexahydrophthalazin-1-yl)oxy)phenyl)-3,5-dioxo-2,3,4,5-tetrahydro-1,2,4-triazine-6-carbonitrile (Compound 5)

The synthetic route of Embodiment 1 was employed, except that the raw material 3,4,5,6-tetrahydrophthalic anhydride (compound 1a) in Step 1 was replaced with 4-methyl-4,5,6,7-tetrahydroisophenylfuran-1,3-dione (compound 5f), to produce the title product 2-(3,5-dichloro-4-((5-methyl-4-oxo-3,4,5,6,7,8-hexahydrophthalazin-1-yl)oxy)phenyl)-3,5-dioxo-2,3,4,5-tetrahydro-1,2,4-triazine-6-carbonitrile (compound 5).

MS m/z (ESI): 460.1 [M+1]

Embodiment 6: Preparation of 2-(3,5-dichloro-4-((5,5-dimethyl-4-oxo-3,4,5,6,7,8-hexahydrophthalazin-1-yl)oxy)phenyl)-3,5-dioxo-2,3,4,5-tetrahydro-1,2,4-triazine-6-carbonitrile

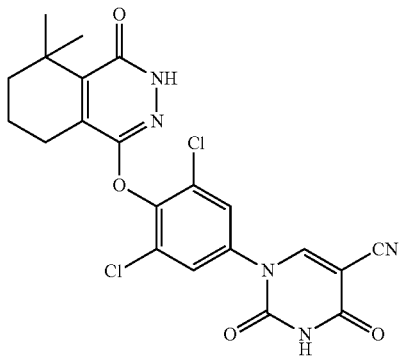

The synthetic route of Embodiment 5 was employed, except that the raw material 2-methylcyclohexanone (compound 5a) in Step 1 was replaced with 2,2-dimethylcyclohexanone, to produce the title product 2-(3,5-dichloro-4-((5,5-dimethyl-4-oxo-3,4,5,6,7,8-hexahydrophthalazin-1-yl)oxy)phenyl)-3,5-dioxo-2,3,4,5-tetrahydro-1,2,4-triazine-6-carbonitrile (compound 6).

MS m/z (ESI): 474.1 [M+1]

Embodiment 7: Preparation of 2-(3,5-dichloro-4-((7-methyl-1-oxo-2,5,6,7-tetrahydro-1H-cyclopenta[d]pyridazin-4-yl)oxy)phenyl)-3,5-dioxo-2,3,4,5-tetrahydro-1,2,4-triazine-6-carbonitrile (Compound 7)

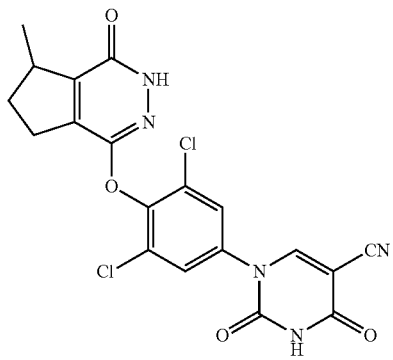

The synthetic route of Embodiment 5 was employed, except that the raw material 2-methylcyclohexanone (compound 5a) in Step 1 was replaced with 2-methylcyclopentanone, to produce the title product 2-(3,5-dichloro-4-((7-methyl-1-oxo-2,5,6,7-tetrahydro-1H-cyclopenta[d]pyridazin-4-yl)oxy)phenyl)-3,5-dioxo-2,3,4,5-tetrahydro-1,2,4-triazine-6-carbonitrile (compound 7).

MS m/z (ESI): 446.0 [M+1]

Embodiment 8: Preparation of 2-(3,5-dichloro-4-((7-ethyl-1-oxo-2,5,6,7-tetrahydro-1H-cyclopenta[d]pyridazin-4-yl)oxy)phenyl)-3,5-dioxo-2,3,4,5-tetrahydro-1,2,4-triazine-6-carbonitrile (Compound 8)

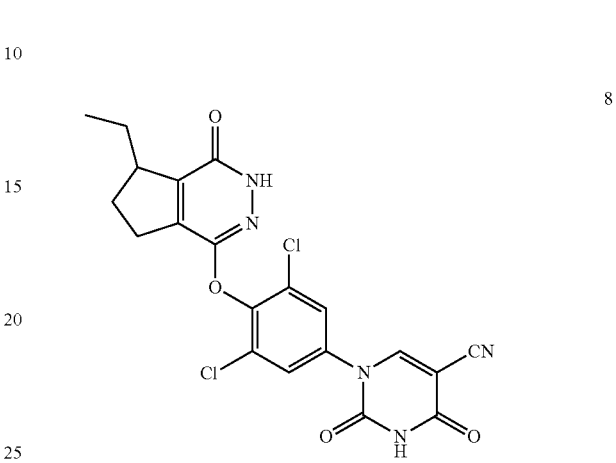

The synthetic route of Embodiment 5 was employed, except that the raw material 2-methylcyclohexanone (compound 5a) in Step 1 was replaced with 2-ethylcyclopentanone, to produce the title product 2-(3,5-dichloro-4-((7-ethyl-1-oxo-2,5,6,7-tetrahydro-1H-cyclopenta[d]pyridazin-4-yl)oxy)phenyl)-3,5-dioxo-2,3,4,5-tetrahydro-1,2,4-triazine-6-carbonitrile (compound 8).

MS m/z (ESI): 460.1 [M+1]

Embodiment 9: Preparation of 2-(3,5-dichloro-4-((4-oxo-3,4-dihydrophthalazin-1-yl)oxy)phenyl)-3,5-dioxo-2,3,4,5-tetrahydro-1,2,4-triazine-6-nitrile (Compound 9)

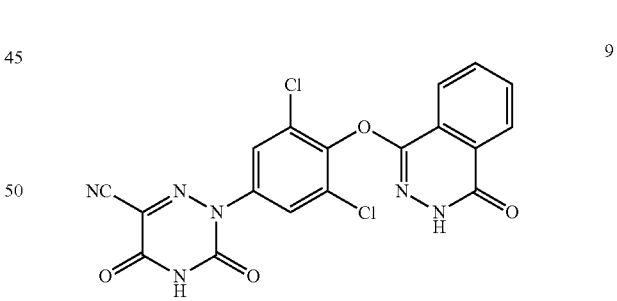

The synthetic route of Embodiment 1 was employed, except that the raw material 1,4-dichloro-5,6,7,8-tetrahydrophthalazine (compound 1c) in Step 3 was replaced with 1,4-dichlorophthalazine, to produce the title product 2-(3,5-dichloro-4-((4-oxo-3,4-dihydrophthalazin-1-yl)oxy)phenyl)-3,5-dioxo-2,3,4,5-tetrahydro-1,2,4-triazine-6-nitrile (compound 9).

$^1$H NMR (400 MHz, DMSO-$d_6$): 12.00 (s, 1H), 8.31 (d, J=8.0 Hz, 1H), 8.26 (d, J=8.0 Hz, 1H), 8.09 (t, J=12.0 Hz 1H), 8.03 (t, J=16.0 Hz 1H), 7.81 (s, 2H).

MS m/z (ESI): 443.0 [M+1].

Embodiment 10: Preparation of 2-(3,5-dichloro-4-((5-chloro-4-oxo-3,4-dihydrophthalazin-1-yl)oxy)phenyl)-3,5-dioxo-2,3,4,5-tetrahydro-1,2,4-triazine-6-nitrile (Compound 10)

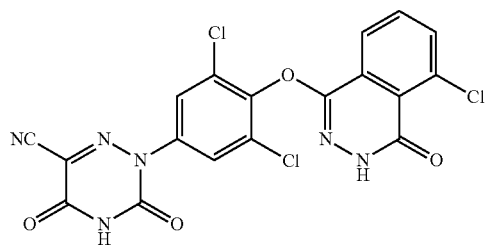

10

The synthetic route of Embodiment 1 was employed, except that the raw material 3,4,5,6-tetrahydrophthalic anhydride (compound 1a) in Step 1 was replaced with 3-chlorophthalic anhydride, to produce the title product 2-(3,5-dichloro-4-((5-chloro-4-oxo-3,4-dihydrophthalazin-1-yl)oxo)phenyl)-3,5-dioxo-2,3,4,5-tetrahydro-1,2,4-triazine-6-nitrile (compound 10)

$^1$H NMR (400 MHz, DMSO-d$_6$): 12.00 (s, 1H), 8.30 (d, J=8.0 Hz, 1H), 8.15 (d, J=8.0 Hz, 1H), 7.95 (m, 1H), 7.80 (s, 2H).

MS m/z (ESI): 477.0 [M+1].

Embodiment 11: Preparation of 2-(3,5-dichloro-4-((5-methyl-4-oxo-3,4-dihydrophthalazin-1-yl)oxy)phenyl)-3,5-dioxo-2,3,4,5-tetrahydro-1,2,4-triazine-6-nitrile (Compound 11)

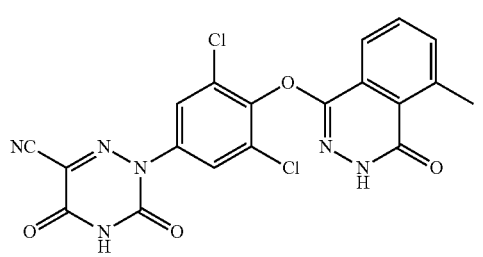

11

The synthetic route of Embodiment 1 was employed, except that the raw material 3,4,5,6-tetrahydrophthalic anhydride (compound 1a) in Step 1 was replaced with 3-methylphthalic anhydride, to produce the title product 2-(3,5-dichloro-4-((5-methyl-4-oxo-3,4-dihydrophthalazin-1-yl)oxo)phenyl)-3,5-dioxo-2,3,4,5-tetrahydro-1,2,4-triazine-6-nitrile (compound 11).

MS m/z (ESI): 456.9 [M+1].

Embodiment 12: Preparation of 2-(3,5-dichloro-4-((4-oxo-3,4,5,6,7,8-hexahydro-5,8-ethanophthalazin-1-yl)oxo)phenyl)-1,2,4-triazine-3,5(2H,4H)-dione (Compound 12)

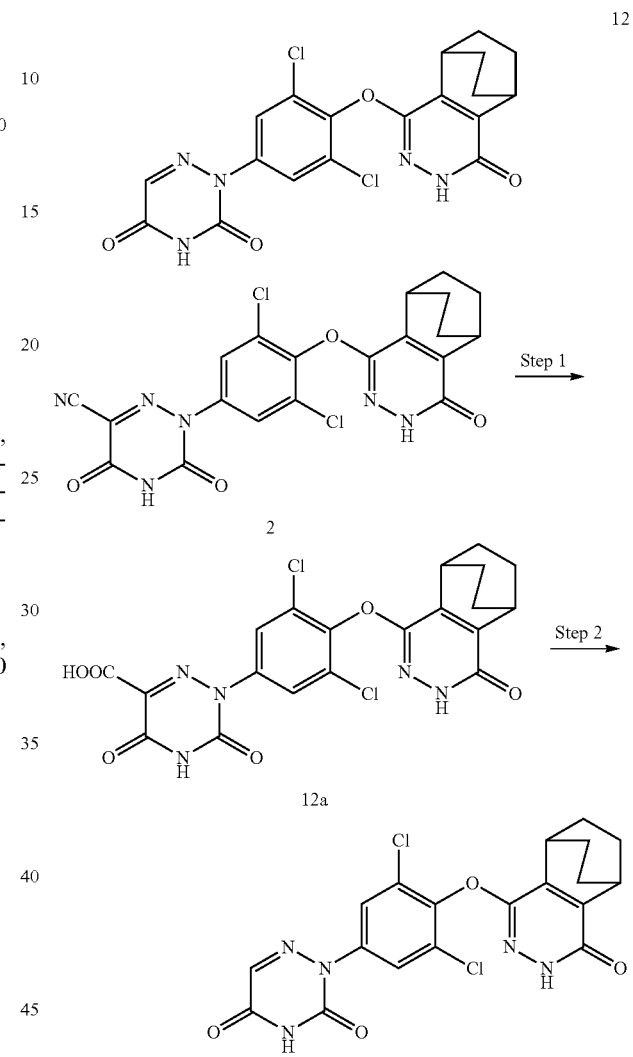

Step 1: Preparation of 2-(3,5-dichloro-4-((4-oxo-3,4,5,6,7,8-hexahydro-5,8-ethanophthalazin-1-yl)oxo)phenyl)-3,5-dioxo-2,3,4,5-tetrahydro-1,2,4-triazine-6-carboxylic acid Acetic acid (4 ml) and concentrated hydrochloric acid (1 ml) were respectively added into the compound 2 (77 mg), heated to a temperature of 120° C., stirred for 5 h, and cooled. The reaction solution was diluted with water. The solid obtained was filtered, washed with water, and washed with petroleum ether, to obtain a solid compound 12a (35 mg) directly used in the next reaction.

Step 2: Preparation of 2-(3,5-dichloro-4-((4-oxo-3,4,5,6,7,8-hexahydro-5,8-ethanophthalazin-1-yl)oxo)phenyl)-1,2,4-triazine-3,5(2H,4H)-dione Mercaptoacetic acid (2 ml) was added into the compound 12a (35.0 mg), and the mixture was heated to a temperature of 170° C. and stirred for 2 h. The mixture was cooled, adjusted to pH 8 with a 1N aqueous sodium hydroxide solution, and extracted 3 times with ethyl acetate. Organic phases were combined. The solvent was removed under reduced pressure, and a compound 12 (10.0 mg) was obtained by separation and purification through thin-layer chromatography (DCM:MeOH=8:1).

$^1$H NMR (400 MHz, DMSO-d$_6$): 12.10 (s, 1H), 7.77 (s, 2H), 7.33 (s, 1H), 2.01 (m, 2H), 1.93-1.75 (m, 4H), 1.39-1.27 (m, 4H).

MS m/z (ESI): 448.0 [M+1].

Embodiment 13: Preparation of 2-(3,5-dichloro-4-((7,7-dimethyl-1-oxo-2,5,6,7-tetrahydro-1H-cyclopentyl[d]pyridazin-4-yl)oxo)phenyl)-1,2,4-triazine-3,5(2H,4H)-dione (Compound 13)

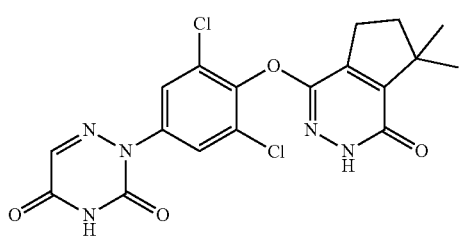

The synthetic route of Embodiment 12 was employed, except that the raw material 2-(3,5-dichloro-4-((4-oxo-3,4,5,6,7,8-hexahydro-5,8-ethanophthalazin-1-yl)oxy)phenyl)-3,5-dioxo-2,3,4,5-tetrahydro-1,2,4-triazine-6-nitrile (compound 2) in Step 1 was replaced with 2-(3,5-dichloro-4-((7,7-dimethyl-1-oxo-2,5,6,7-tetrahydro-1H-cyclopenta[d]pyridazin-4-yl)oxy)phenyl)-3,5-dioxo-2,3,4,5-tetrahydro-1,2,4-triazine-6-carbonitrile (compound 4), to produce the title product 2-(3,5-dichloro-4-((7,7-dimethyl-1-oxo-2,5,6,7-tetrahydro-1H-cyclopentyl[d]pyridazin-4-yl)oxo)phenyl)-1,2,4-triazine-3,5(2H,4H)-dione (compound 13).

$^1$H NMR (400 MHz, DMSO-d$_6$): 12.02 (s, 1H), 7.77 (s, 2H), 7.35 (s, 1H), 2.94-2.90 (m, 2H), 1.99-1.95 (m, 2H), 1.32 (d, 6H).

MS m/z (ESI): 436.0 [M+1].

Embodiment 14: Preparation of 2-(3,5-dichloro-4-((4-oxo-3,4-dihydrophthalazin-1-yl)oxo)phenyl)-1,2,4-triazine-3,5-(2H,4H)dione (Compound 14)

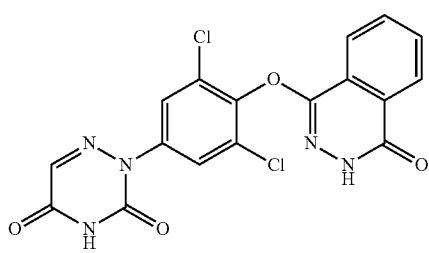

The synthetic route of Embodiment 12 was employed, except that the raw material 2-(3,5-dichloro-4-((4-oxo-3,4,5,6,7,8-hexahydro-5,8-ethanophthalazin-1-yl)oxy)phenyl)-3,5-dioxo-2,3,4,5-tetrahydro-1,2,4-triazine-6-nitrile (compound 2) in Step 1 was replaced with 2-(3,5-dichloro-4-((4-oxo-3,4-dihydrophthalazin-1-yl)oxo)phenyl)-3,5-dioxo-2,3,4,5-tetrahydro-1,2,4-triazine-6-nitrile (compound 9), to produce the title product 2-(3,5-dichloro-4-((4-oxo-3,4-dihydrophthalazin-1-yl)oxo)phenyl)-1,2,4-triazine-3,5-(2H,4H)dione (compound 14).

$^1$H NMR (400 MHz, DMSO-d$_6$): 12.00 (s, 1H), 8.30-8.23 (m, 2H), 8.09-7.99 (m, 2H), 7.18 (s, 1H).

MS m/z (ESI): 418.0 [M+1].

Embodiment 15: Preparation of 2-(3,5-dichloro-4-((5-fluoro-4-oxo-3,4-dihydrophthalazin-1-yl)oxy)phenyl)-3,5-dioxo-2,3,4,5-tetrahydro-1,2,4-triazine-6-nitrile (Compound 15)

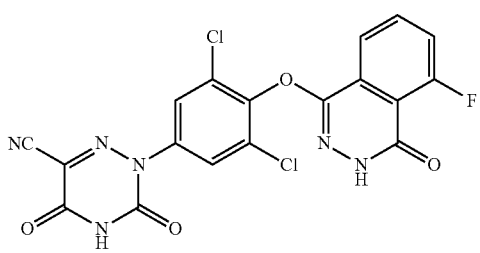

The synthetic route of Embodiment 1 was employed, except that the raw material 3,4,5,6-tetrahydrophthalic anhydride (compound 1a) in Step 1 was replaced with 3-fluorophthalic anhydride, to produce the title product 2-(3,5-dichloro-4-((5-fluoro-4-oxo-3,4-dihydrophthalazin-1-yl)oxy)phenyl)-3,5-dioxo-2,3,4,5-tetrahydro-1,2,4-triazine-6-nitrile (compound 15).

MS m/z (ESI): 461.0 [M+1].

Embodiment 16: Preparation of 2-(3,5-dichloro-4-((4-oxo-3,4,5,6,7,8-hexahydrophthalazin-1-yl)oxo)phenyl)-6-methyl-1,2,4-triazine-3,5(2H,4H)-dione (Compound 16)

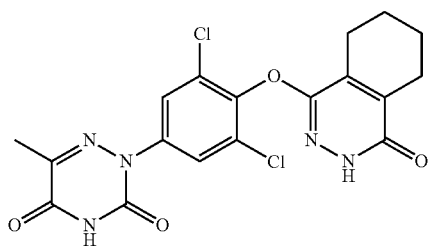

Step 1: Preparation of 4-(2,6-dichloro-4-iodophenoxy)-5,6,7,8-tetrahydrophthalazin-1(2H)-one (Compound 16a)

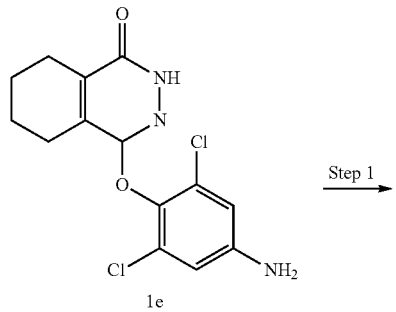

1e

Under ice bath conditions, water (4 ml) and concentrated hydrochloric acid (2 ml) were successively added into 1e (100 mg), followed by the dropwise addition of a solution of sodium nitrite (30 mg) in water (2 ml). The reaction was stirred for 1 h under the maintained ice bath conditions. Potassium iodide (104 mg) was added dropwise, and the mixture was warmed up to room temperature and stirred for 16 h. The mixture was extracted with dichloromethane, and the solvent was removed under reduced pressure, to obtain a yellow solid 16a (100 mg), directly used in the next reaction.

Step 2: Preparation of 2-(3,5-dichloro-4-((4-oxo-3,4,5,6,7,8-hexahydrophthalazin-1-yl)oxo)phenyl)-6-methyl-1,2,4-triazine-3,5(2H,4H)-dione (Compound 16)

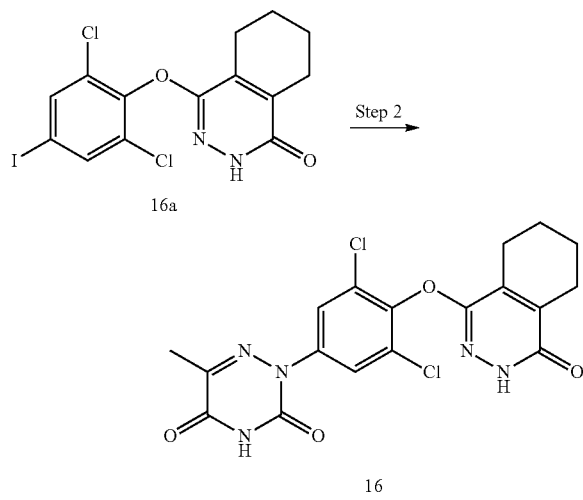

N,N-dicarbonamide (2.0 ml) was added into a mixture of the compound 16a (20 mg), 6-azathymine (6.6 mg), cuprous iodide (8.9 mg), and potassium carbonate (30 mg), and the system was heated to a temperature of 120° C. and stirred for 12 h. The system was cooled, filtered, and separated from water through the addition of ethyl acetate. The solvent was removed from the organic phase under reduced pressure, and a compound 16 (5.0 mg) was obtained by separation and purification through thin-layer chromatography (DCM: MeOH=8:1).

MS m/z (ESI): 436.1 [M+1].

Embodiment 17: Preparation of 2-(3,5-dichloro-4-((4-oxo-3,4,5,6,7,8-hexahydrophthalazin-1-yl)oxo)phenyl)-6-isopropyl-1,2,4-triazine-3,5(2H,4H)-dione (Compound 17)

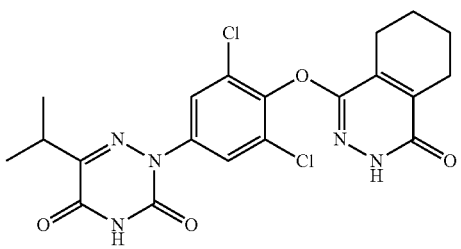

The synthetic route of Embodiment 16 was employed, except that the raw material 6-azathymine in Step 2 was replaced with 6-isopropyl-1,2,4-triazine-3,5(2H,4H)-dione (prepared by employing the well known method "*Chemistry and Biodiversity*, 2012, 9(3) 536-556"), to produce the title product 2-(3,5-dichloro-4-((4-oxo-3,4,5,6,7,8-hexahydrophthalazin-1-yl)oxo)phenyl)-6-isopropyl-1,2,4-triazine-3,5(2H,4H)-dione (compound 17).

MS m/z (ESI): 464.1 [M+1].

Embodiment 18: Preparation of 6-cyclopropyl-2-(3,5-dichloro-4-((4-oxo-3,4,5,6,7,8-hexahydrophthalazin-1-yl)oxo)phenyl)-1,2,4-triazine-3,5(2H,4H)-dione (Compound 18)

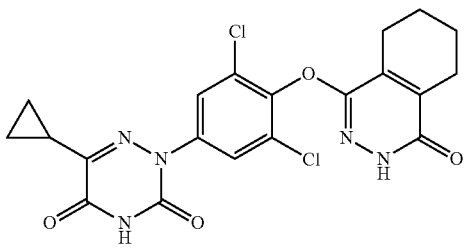

The synthetic route of Embodiment 16 was employed, except that the raw material 6-azathymine in Step 2 was replaced with 6-cyclopropyl-1,2,4-triazine-3,5(2H,4H)-dione (prepared by employing the well known method found in "*Collection of Czechoslovak Chemical Communications*, 1975, 40, 1038-1041"), to produce the title product 2-(3,5-dichloro-4-((4-oxo-3,4,5,6,7,8-hexahydrophthalazin-1-yl)oxo)phenyl)-6-cyclopropyl-1,2,4-triazine-3,5(2H,4H)-dione (compound 18).

MS m/z (ESI): 462.1 [M+1].

Embodiment 19: Preparation of 2-(3,5-dichloro-4-((4-oxo-3,4-dihydrophthalazin-1-yl)oxo)phenyl)-6-methyl-1,2,4-triazine-3,5(2H,4H)-dione (Compound 19)

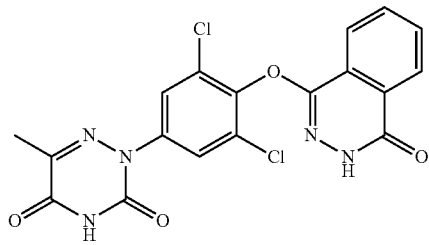

Step 1: Preparation of 3,5-dichloro-4-((4-chlorophthalazin-1-yl)oxo)aniline (Compound 19a)

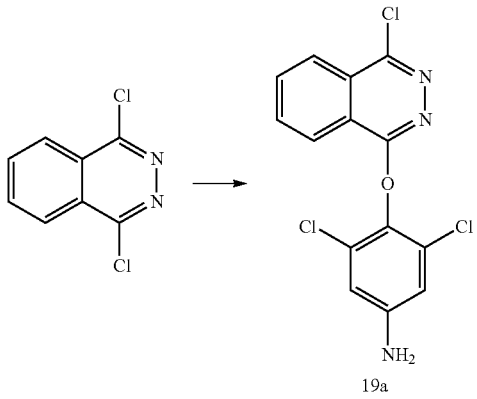 [SMILES: Clc1nnc(Cl)c2ccccc12 ; Nc1cc(Cl)c(Oc2nnc(Cl)c3ccccc23)c(Cl)c1]

The synthetic route of Intermediate 1d in Step 3 of Embodiment 1 was employed, except that 1,4-dichloro-5,6,7,8-tetrahydrophthalazine (compound 1e) was replaced with 1,4-dichlorophthalazine, to produce the title product 3,5-dichloro-4-((4-chlorophthalazin-1-yl)oxo)aniline (compound 19a).

Step 2: Preparation of 4-(4-amino-2,6-dichlorophenoxy)phthalazin-1(2H)-one (Compound 19b)

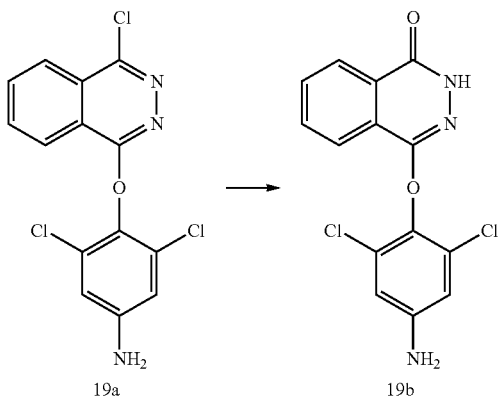 [SMILES: Nc1cc(Cl)c(Oc2nnc(Cl)c3ccccc23)c(Cl)c1 ; Nc1cc(Cl)c(Oc2n[nH]c(=O)c3ccccc23)c(Cl)c1]

The synthetic route of Intermediate 1e in Step 4 of Embodiment 1 was employed, except that 3,5-dichloro-4-((4-chloro-5,6,7,8-tetrahydrophthalazin-1-yl)oxy)aniline (compound 1d) was replaced with 3,5-dichloro-4-((4-chlorophthalazin-1-yl)oxo)aniline (compound 19a), to produce the title product 4-(4-amino-2,6-dichlorophenoxy)phthalazin-1(2H)-one (compound 19b).

Step 3: Preparation of 2-(3,5-dichloro-4-((4-oxo-3,4-dihydrophthalazin-1-yl)oxo)phenyl)-6-methyl-1,2,4-triazine-3,5(2H,4H)-dione (Compound 19)

The synthetic route of Embodiment 16 was employed, except that 4-(2,6-dichloro-4-iodophenoxy)-5,6,7,8-tetrahydrophthalazin-1(2H)-one (compound 16a) in Step 1 was replaced with the compound 4-(4-amino-2,6-dichlorophenoxy)phthalazin-1(2H)-one (compound 19b), to produce the title product 2-(3,5-dichloro-4-((4-oxo-3,4-dihydrophthalazin-1-yl)oxo)phenyl)-6-methyl-1,2,4-triazine-3,5(2H,4H)-dione (compound 19).

MS m/z (ESI): 432.0 [M+1].

Embodiment 20: Preparation of 2-(3,5-dichloro-4-((6-methyl-4-oxo-3,4-dihydrophthalazin-1-yl)oxy)phenyl)-3,5-dioxo-2,3,4,5-tetrahydro-1,2,4-triazine-6-nitrile (Compound 20)

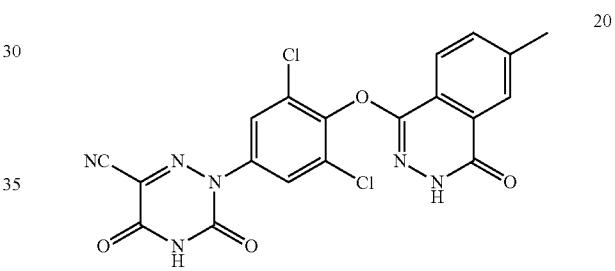

The synthetic route of Embodiment 1 was employed, except that the raw material tetrahydrophthalic anhydride (1a) in Step 1 was replaced with 4-methylphthalic anhydride, to produce the title product 2-(3,5-dichloro-4-((6-methyl-4-oxo-3,4-dihydrophthalazin-1-yl)oxy)phenyl)-3,5-dioxo-2,3,4,5-tetrahydro-1,2,4-triazine-6-nitrile (compound 20).

MS m/z (ESI): 457.0 [M+1].

Embodiment 21: Preparation of 2-(3,5-dichloro-4-((6-chloro-4-oxo-3,4-dihydrophthalazin-1-yl)oxy)phenyl)-3,5-dioxo-2,3,4,5-tetrahydro-1,2,4-triazine-6-nitrile (Compound 21)

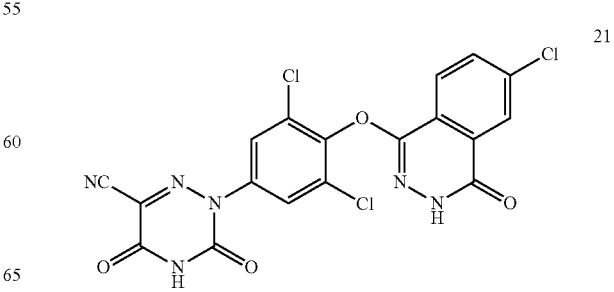

The synthetic route of Embodiment 1 was employed, except that the raw material tetrahydrophthalic anhydride (1a) in Step 1 was replaced with 4-chlorophthalic anhydride, to produce the title product 2-(3,5-dichloro-4-((6-chloro-4-oxo-3,4-dihydrophthalazin-1-yl)oxy)phenyl)-3,5-dioxo-2,3,4,5-tetrahydro-1,2,4-triazine-6-nitrile (compound 21).

MS m/z (ESI): 477.0 [M+1].

Test Embodiment 1: Binding Force of the Compound to TRα Test

1. Main Experimental Materials and Apparatuses:
   Envision 2104 microplate reader;
   Biotin-SRC2-2 coactivator peptide, commercially available from Sangon Biotech (Shanghai) Co., Ltd.;
   TRα LBD, GST, commercially available from ThermoFisher (Art. No. PV4762);
   Europium binding anti-glutathione antibody, commercially available from Cisbio (Art. No. 61GSTKLB); and
   Streptavidin-D2, commercially available from Cisbio (Art. No. 610SADAB)
2. Preparation and Treatment of Compounds
2.1 Preparation of Stock Solution of the Compound in Dimethyl Sulfoxide
   All compounds were dissolved in dimethyl sulfoxide to prepare a 10 mmol stock solution.
2.2 Compound Storage
   After the compounds were dissolved in dimethyl sulfoxide, the solution can be stored for 3 months in a desiccator at room temperature. For long-term storage, compounds shall be placed into a refrigerator at −20° C.
3. Experimental Steps
3.1 Preparation of 1× Reaction Buffer
3.2 Compound Screening:
   a) 100% dimethyl sulfoxide was used to dilute the positive drug triiodothyronine (T3) from 10 mmol (100×) or the compound to be tested from 1 mmol (100×), at an equal ratio of 1:3, for a total of 10 concentrations.
   b) a 4× concentration gradient diluted compound was prepared with a 1× reaction buffer.
   c) 5 µl of the 4× concentration gradient diluted compound was added into a 384-well test plate.
   d) 4× TRα LBD and 4× RXRα were prepared with the 1× reaction buffer.
   e) 5 µl of 4× TRα LBD and 4× RXRα were added into the 384-well test plate.
   f) 2× biotin-SRC2-2, 2× Europium binding anti-glutathione antibody, and 2× streptavidin-d2 were prepared with the 1× reaction buffer.
   g) 10 µl of a 2× mixed solution (referring to Step f) was added into the 384-well test plate.
   h) The 384-well test plate was centrifugated for 1000 revolutions within 1 min in a centrifuge.
   i) Incubation at room temperature was performed for 1 h while protected from light.
   j) The fluorescence signal values of each well of the 384-well test plate at the wavelength of 665 nm and 615 nm were recorded with the Envision 2104 microplate reader, and the fluorescence ratio of 665 nm/615 nm was calculated.

4. Data Analysis
4.1 Calculation of Relative Ratio ($Ratio_{665\ nm/615\ nm} - Ratio_{blank}$) of Each Well
4.2 the Activity Percentage was Calculated as Follows:

$$\text{Activity (\%)} = \left[ \frac{Ratio_{compound} - \overline{Ratio}_{blank}}{\overline{Ratio}_{positive} - \overline{Ratio}_{blank}} \right] * 100$$

$\overline{Ratio}_{compound}$: average of relative ratios of wells of embodiment compounds
$\overline{Ratio}_{positive}$: average of relative ratios of all positive control wells
$\overline{Ratio}_{blank}$: average of relative ratios of all negative control wells 4.3 Curve Plotting and EC50 Calculation:
   EC50 was calculated by using Graphpad 5.0 through the nonlinear regression method to fit the relationship between the activity (%) and the logarithm concentration of the compound.

$Y = \text{bottom} + (\text{top} - \text{bottom})/(1 + 10^{((Log\ EC50 - X) \times slope)})$ X: Logarithm concentration of the compound Y: Percentage activity Particular test data are shown in Table 1 as follows.

Test Embodiment 2: Evaluation of the Agonistic Activity of the Compound Toward TRα

1. Main Experimental Materials and Apparatuses:
   Envision 2104 microplate reader
   HEK293T cell line, commercially available from ATCC (Art. No.: CRL-3216)
   pGL4.35[luc2P/9XGAL4 UAS/Hygro], commercially available from Promega (Art. No.: E1370)
   pBIND-TRα plasmid, from Pharmaron
   pBIND-RXRα plasmid, from Pharmaron
   LipoLTX transfection agent, commercially available from ThermoFisher (Art. No.: 15338-100)
2. Compound Preparation
2.1 Compound Dissolution
   The compound powder was prepared into a 10 mmol stock solution in dimethyl sulfoxide according to the standard scheme.
2.2 Compound Storage
   All compounds dissolved in dimethyl sulfoxide were stored in a desiccator at room temperature for a short term, or stored at −20° C. for a long term.
2.3 Preparation of Experimental Compounds
2.3.1 all the Compounds to be Tested were Diluted with Dimethyl Sulfoxide at a 3-Fold Gradient, in 10 Dilution Gradients, Starting from the Initial Concentration of 10 µmol.
2.3.2 the Positive Control Triiodothyronine (T3) was Diluted with Dimethyl Sulfoxide at a 3-Fold Gradient, in 10 Dilution Gradients, Starting from the Initial Concentration of 16.67 µMol.
2.3.3 A 166.7× Positive Control (16.67 Gmol, Triiodothyronine (T3)) and a 166.7× Negative Control (100% Dimethyl Sulfoxide) were Prepared.
2.4 the Compound Plate was Closed and Shaken for 5 Min.
3 Experiment Process
3.1 Cell Suspension Preparation and Plate Seeding
   a) All cells were cultured according to the ATCC standard operation, and HEK293T was tested in the exponential growth period;

b) The medium was discarded;
c) The cells were washed twice with a phosphate buffer;
d) A trypsinization solution was added to digest the cells, and the digestion was terminated with a complete medium;
e) The cells were collected and counted, and only when the cell viability was greater than 90% could the experiment be carried out;
f) $2.5 \times 10^6$ HEK293-LUC cells were seeded into a 60-mm cell culture dish; and
g) The culture dish with cells seeded was placed into an incubator at 37° C. and 5% $CO_2$ and cultured overnight.

3.2 Cell Transfection
a) The LipoLTX transfection agent was placed at room temperature for balancing;
b) 6 µl of Plus agent and 6 µg of DNA were added into 250 µl of Opti-MEM™ medium without contacting the tube wall, and they were mixed uniformly through blowing and pipetting by a pipetting gun, and Plasmid: 2.5 µg of pBIND-TRα, 2.5 µg of pBIND-RXRα and 1 µg of pGL4.35 plasmid were respectively added therein;
c) 12 µl of Lipo LTX and 250 µl of Opti-MEM™ medium were added without contacting the tube wall, and they were mixed uniformly through blowing and pipetting by a pipetting gun;
d) the agent mixed with DNA Plus (see Step 3.2.b) was added into the diluted LipoLTX (see Step 3.2.c) transfection agent, and stood still for 15 min at room temperature;
e) the transfection agent mixed with DNA was added to a 60-mm cell culture dish (see Step 3.1); and
f) the culture dish was placed into an incubator at 37° C. and 5% $CO_2$ and cultured for 5 h.

3.3 Compound Treatment
a) 150 nl of the diluted compound (see Step 2.3) was transferred by Echo550 to a cell culture plate (6007680-50, PE);
b) the cells (see Step 3.2) were seeded to a 384 cell culture plate (6007680-50, PE), with 15,000 cells and 25 µl of the medium containing 5% fetal bovine serum per well; and
c) the cells were cultured overnight in an incubator at 37° C. and 5% $CO_2$.

3.4 Compound Detection
a) The Steady-Glo™ detection agent was placed at room temperature;
b) the 384 cell plate (see Step 3.3) was placed at room temperature;
c) 25 µl of the Steady-Glo™ detection agent per well was added into the cell culture plate (see Step 3.4b);
d) the plate was placed on a shaker and shaken for 5 min while protected from light; and
e) the chemiluminescence value was detected with the Envision 2104 microplate reader.

4. Data Analysis
4.1 Calculation of Activity (%):

$$\text{Activity } (\%) = \left[ \frac{RLU_{compound} - \overline{RLU}_{blank}}{\overline{RLU}_{positive} - \overline{RLU}_{blank}} \right] \times 100$$

RLU: Fluorescence generated
$\overline{RLU}_{compound}$: Well average of embodiment compounds
$\overline{RLU}_{positive}$: positive control average
$\overline{RLU}_{blank}$: negative control average 4.2 EC50 Calculation and Plotting of Dose-Effect Curve of the Compound
EC50 of the compound was calculated by using Graphpad 5.0 to fit the activity (%) and the logarithm concentration of the compound.

$$Y = \text{bottom} + (\text{top} - \text{bottom})/(1 + 10\textasciicircum((\text{Log IC50} - X) \times \text{slope}))$$

X: Logarithm concentration of the compound Y: Percentage inhibition rate
Particular test data are shown in Table 1 as follows.

Test Embodiment 3: Binding Force of the Compound to TRβ Test

1. Main Experimental Material and Apparatus:
Envision 2104 microplate reader,
Biotin-SRC2-2 coactivator peptide, commercially available from Sangon Biotech (Shanghai) Co., Ltd.
TRβ LBD, GST, commercially available from ThermoFisher (Art. No. PV4762)
Europium binding anti-glutathione antibody, commercially available from Cisbio (Art. No. 61GSTKLB)
Streptavidin-D2, commercially available from Cisbio (Art. No. 610SADAB)

2. Preparation and Treatment of Compounds
2.1 Preparation of Stock Solution of the Compound in Dimethyl Sulfoxide
All compounds were dissolved in dimethyl sulfoxide to prepare a 10 mmol stock solution.
2.2 Compound Storage
After the compounds were dissolved in dimethyl sulfoxide, the solution can be stored for 3 months in a desiccator at room temperature. For long-term storage, compounds shall be placed into a refrigerator at −20° C.

3. Experimental Steps
3.1 Preparation of 1× Reaction Buffer
3.2 Compound Screening:
a) 100% dimethyl sulfoxide was used to dilute the positive drug triiodothyronine (T3) from 10 µmol (100×) or the compound to be tested from 1 mmol (100×), at an equal ratio of 1:3, totally in 10 concentrations;
b) A 4× concentration gradient diluted compound was prepared with a 1× reaction buffer;
c) 5 µl of the 4× concentration gradient diluted compound was added into a 384-well test plate;
d) 4× TRP LBD and 4× RXRβ were prepared with the 1× reaction buffer;
e) 5 µl of 4× TRβ LBD and 4× RXRβ were added into the 384-well test plate;
f) 2× biotin-SRC2-2, 2× Europium binding anti-glutathione antibody and 2× streptavidin-d2 were prepared with the 1× reaction buffer;
g) 10 µl of a 2× mixed solution (referring to Step f) was added into the 384-well test plate;
h) The 384-well test plate was centrifugated for 1000 revolutions within 1 min in a centrifuge;
i) Incubation at room temperature was performed for 1 h, while protected from light; and
j) The fluorescence signal values of each well of the 384-well test plate at the wavelength of 665 nm and 615 nm were recorded with the Envision 2104 microplate reader, and the fluorescence ratio of 665 nm/615 nm was calculated.

4. Data Analysis 4.1 Calculation of Relative Ratio (Ratio$_{665\,nm/615\,nm}$−Ratio$_{blank}$) of Each Well 4.2 the Activity Percentage was Calculated as Follows:

$$\text{Activity (\%)} = \left[\frac{\text{Ratio}_{compound} - \overline{\text{Ratio}}_{blank}}{\overline{\text{Ratio}}_{positive} - \overline{\text{Ratio}}_{blank}}\right] \times 100$$

$\overline{\text{Ratio}}_{compound}$: average of relative ratios of wells of embodiment compounds $\overline{\text{Ratio}}_{positive}$: average of relative ratios of all positive control wells $\overline{\text{Ratio}}_{blank}$: average of relative ratios of all negative control wells 4.3 Curve Plotting and EC50 Calculation:

EC50 was calculated by using Graphpad 5.0 through the nonlinear regression method to fit the relationship between the activity (%) and the logarithm concentration of the compound.

$$Y = \text{bottom} + (\text{top}-\text{bottom})/(1+10\^((\text{Log EC50}-X) \times \text{slope}))$$

X: Logarithm concentration of the compound Y: Percentage activity

Particular test data are shown in Table 1 as follows.

| | IC50 | | |
|---|---|---|---|
| Embodiments | THRβ binding force (μM) | THRα binding force (μM) | THRα/β selectivity (factor) |
| Embodiment 1 | 1.23 | >10 | >8.1 |
| Embodiment 2 | 2.33 | >10 | >4.29 |
| Embodiment 3 | 5.2 | >10 | >1.92 |
| Embodiment 4 | 0.36 | 4.3 | >11.9 |
| Embodiment 9 | 0.17 | >10 | >58.8 |
| Embodiment 10 | 1.47 | >10 | >6.80 |
| Embodiment 11 | 1.78 | >10 | 5.61 |
| Embodiment 12 | 0.80 | 0.2 | 0.25 |
| Embodiment 13 | 0.17 | 1.22 | 7.17 |
| Embodiment 14 | 0.262 | | |
| Comparative Compound 53 | 0.26 | 5.0 | 19.2 |
| T3 | 0.00052 | 0.00026 | |

Conclusion: compared with the disclosed comparative compound 53, some of the compounds according to the present invention unexpectedly showed high THRβ activity (<0.2 μM), and some of the compounds showed higher selectivity to THRα than the comparative compound 53.

Test Embodiment 4: Evaluation of Agonistic Activity of the Compound Toward the TRβ Receptor Experiment Summary: TRβ-LBD and RXRα-LBD coding sequences were inserted into a pBTND plasmid (Promega, E1581) respectively. The expression vector and the reporter vector (pGL4.35 carrying a luciferase reporter gene driven by a stable integrated GAL4 promoter) were co-expressed in the host cell. When the agonist binds to the corresponding chimeric receptor, the chimeric receptor binds to the GAL4 binding site on the reporter gene vector and stimulates the reporter gene expression. According to the intensity of chemiluminescence signals, the agonistic activity of the compound toward the TRP receptor was determined.

Experimental Materials and Apparatuses:
Envision 2104 microplate reader
HEK293T cell line, commercially available from ATCC (Art. No.: CRL-3216)
pGL4.35[luc2P/9XGAL4 UAS/Hygro], commercially available from Promega (Art. No.: E1370)
pBIND-TR β plasmid, from Pharmaron
pBIND-RXRα plasmid, from Pharmaron
LipoLTX transfection agent, commercially available from ThermoFisher (Art. No.: 15338-100)
Steady-Glo™ luciferase detection kit, commercially available from Promega (Art. No.: E2520)

2.3 Preparation of Experimental Compounds

All the compounds to be tested were diluted with dimethyl sulfoxide at a 3-fold gradient, in 10 dilution gradients, starting from the initial concentration of 10 mmol.

The positive control triiodothyronine (T3) was diluted with dimethyl sulfoxide at a 3-fold gradient, in 10 dilution gradients, starting from the initial concentration of 16.67 μmol.

A 166.7× positive control (16.67 μmol, triiodothyronine (T3)) and a 166.7× negative control (100% dimethyl sulfoxide) were prepared.

The compound plate was closed and shaken for 5 min.

Experiment Process 3.1 Cell Suspension Preparation and Plate Seeding a) All cells were cultured according to the ATCC standard operation, and HEK293T was tested in the exponential growth period;
b) The medium was discarded;
c) The cells were washed twice with a phosphate buffer;
d) A trypsinization solution was added to digest the cells, and the digestion was terminated with a complete medium;
e) The cells were collected and counted, and only when the cell viability was greater than 90% could the experiment be carried out;
f) $2.5 \times 10^6$ HEK293-LUC cells were seeded into a 60-mm cell culture dish; and
g) The culture dish with cells seeded was placed into an incubator at 37° C. and 5% $CO_2$ and cultured overnight.

3.2 Cell Transfection a) The LipoLTX transfection agent was placed at room temperature for balancing;
b) 6 μl of Plus agent and 6 μg of DNA were added into 250 μl of an Opti-MEM™ medium without contacting the tube wall, and they were mixed uniformly through blowing and pipetting by a pipetting gun; plasmid: 2.5 μg of pBIND-TRP, 2.5 μg of pBIND-RXRα and 1 μg of pGL4.35 plasmid
c) 12 μl of Lipo LTX and 250 μl of Opti-MEM™ medium were added without contacting the tube wall, and they were mixed uniformly through blowing and pipetting by a pipetting gun;
d) the agent mixed with DNA plus (see Step 3.2.b) was added into the diluted LipoLTX (see Step 3.2.c) transfection agent and stood still for 15 min at room temperature; e) the transfection agent mixed with DNA was added to a 60-mm cell culture dish (see Step 3.1); and
f) the culture dish was placed into an incubator at 37° C. and 5% $CO_2$ and cultured for 5 h.

3.3 Compound Treatment a) 150 nl of the diluted compound (see Step 2.3) was transferred by Echo550 to a cell culture plate (6007680-50, PE);

b) the cells (see Step 3.2) were seeded to a 384 cell culture plate (6007680-50, PE) with 15,000 cells and 25 μl of the medium per well; and c) the cells were cultured overnight in an incubator at 37° C. and 5% $CO_2$.

3.4 Compound Detection a) The Steady-Glo™ detection agent was placed at room temperature;

b) the 384 cell plate (see Step 3.3) was placed at room temperature;

c) 25 μl of the Steady-Glo™ detection agent per well was added into the cell culture plate (see Step 3.4b);

d) the plate was placed on a shaker and shaken for 5 min while protected from light; and e) the chemiluminescence value was detected with the Envision 2104 microplate reader.

Data Analysis 4.1 Calculation of Activity (%):

$$\text{Activity (\%)} = \left[ \frac{RLU_{compound} - \overline{RLU}_{blank}}{\overline{RLU}_{positive} - \overline{RLU}_{blank}} \right] \times 100$$

RLU: fluorescence generated $\overline{RLU}_{compound}$: Well average of embodiment compounds $\overline{RLU}_{positive}$: positive control average $RLU_{blank}$: negative control average 4.2 EC50 Calculation and Plotting of Dose-Effect Curve of the Compound EC50 of the compound was calculated by using Graphpad 5.0 to fit the activity (%) and the logarithm concentration of the compound.

$Y$=bottom+(top−bottom)/(1+10^((Log IC50−X)× slope))

X: Logarithm concentration of the compound Y: Percentage inhibition rate

Table 2: the agonistic activity of the compound of the present invention toward the thyroxine receptor beta is shown as follows:

|  | $EC_{50}$ | |
| --- | --- | --- |
| Embodiments | THRβ agonistic activity (μM) | THRα agonistic activity (μM) |
| Embodiment 4 | 2.45 | 4.25 |
| Embodiment 9 | 1.75 | 3.98 |
| Embodiment 12 | 0.79 | 1.08 |
| Embodiment 13 | 0.097 | 0.123 |
| Comparative Compound 53 | 2.48 | 4.57 |
| T3 | 0.001 | 0.0005 |

Conclusion: the compound of the present invention can activate the downstream signal of the thyroid hormone receptor beta.

Test Embodiment 5: Pharmacokinetic Evaluation

Rats were used as test animals. After intragastric infusion of the compounds from Embodiment 4 and Embodiment 9, the drug concentrations in the plasma of the rats at different times were tested. The pharmacokinetic behaviors of the compounds of the present invention in rats were studied, and the pharmaceutical metabolism characteristics thereof were evaluated. In each group of the embodiment, 3 male SD rats with a similar body weight were selected, and the oral dose was 2 mg/kg in a single dose. Blood was collected at time points of 15 min, 30 min, 1 h, 2 h, 4 h, 6 h, 10 h, and 24 h after administration of the dose to the animals. The LC-MS/MS analytical method was employed to detect the content of the compounds in plasma, and the lower limit of quantification of the method was 20 ng/ml. The metakinetic data analysis software WinNonlin 7.0 was used to generate statistics on VT088 and concentration data of the plasma. The non-compartment model method (NCA) was utilized to calculate the pharmacokinetic parameters, particularly as shown in Table 2 below.

Experiment Scheme:

Experiment Drugs: compounds from Embodiment 4 and Embodiment 9.

Laboratory Animals:

Six healthy male SD rats, commercially available from Shanghai Sippr-Bk Laboratory Animal Co., Ltd., with an animal production license No.: SCXK (Shanghai) 2008-0016, were divided into 2 groups, 3 in each group.

Drug Preparation: a certain amount of the drug was taken and added into a 2% Klucel LF+0.1% Tween 80 aqueous solution, to prepare a clear solution or a uniform suspension.

Dosage: SD rats were fasted overnight and given the drug by intragastric infusion at an administrated dose of 2 mg/kg and an administrated volume of 10 mL/kg each.

Operation: rats were dosed by intragastric infusion with the compounds from Embodiment 4 and Embodiment 9. At least 0.2 mL of blood was collected from the vena caudalis at 15 min, 30 min, 1 h, 2 h, 4 h, 6 h, 10 h, and 24 h before and after the dosage; the blood was then placed in heparinized sample tubes, centrifuged at 4° C. and 3500 rpm for 10 min to separate the plasma. The heparinized sample tubes were then stored at −20° C., and the rats were allowed to eat food 2 h after the dosage.

Determination of contents of the compounds to be tested in the plasma of rats after intragastric infusion of the drugs at different concentrations: the plasma samples were thawed at room temperature, 50 μL each was taken and added into 130 μL of an internal standard working solution (1000 ng/mL, acetonitrile, tolbutamide), and the mixture was whirled for about 1 min and then centrifugated at 4° C. and 13000 rpm for 10 min. 50 μL of the supernatant was taken and mixed with 100 μL of 50% acetonitrile water, and then introduced for LC/MS/MS analysis.

Results of the pharmacokinetic parameters are shown in Table 3.

TABLE 3

| | | | Peak blood drug | | Half- |
| Compound | Dose (mg/kg) | Time to peak (h) | concentration (ng/ml) | Curve area (ng · h/mL) | life (h) |
|---|---|---|---|---|---|
| Embodiment 4 | 2.0 | 5.33 ± 1.15 | 727 ± 183 | 9242 ± 1245 | 5.14 ± 0.83 |
| Embodiment 9 | 2.0 | 4.67 ± 1.15 | 2007 ± 106 | 24790 ± 3704 | 4.56 ± 0.42 |
| Comparative Compound 53 | 2.0 | 5.3 ± 1.15 | 1163 ± 97.1 | 12854 ± 961 | 3.53 ± 0.42 |

Pharmaceutical metabolism data of rats

Conclusion: the compounds of the present invention possess good pharmacokinetic absorption and significant pharmacokinetic advantages. Compared with the reported comparative compound 53, some of the compounds of the present invention unexpectedly show higher Cmax values and exposure amounts at the same dose and preparation. All the above PK results show that, the compounds provided in the present invention have good PK properties and can be used as a therapeutic drug for a metabolism-related disease.

The invention claimed is:

1. A method of synthesizing a compound of Formula (I):

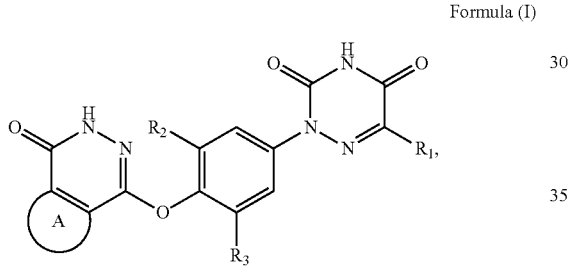

Formula (I)

or a pharmaceutically acceptable salt thereof;
wherein:
Ring A is a $C_{5-10}$ aliphatic ring or a $C_{5-10}$ aromatic ring, each optionally substituted with one or more substituents independently selected from the group consisting of hydrogen, halogen atoms, hydroxy, —$OCF_3$, —$NH_2$, —$NHC_{1-4}$ alkyl, —$N(C_{1-4}alkyl)_2$, —$CONH_2$, —$CONHC_{1-4}$ alkyl, —$CON(C_{1-4}$ alkyl$)_2$, —$NHCOC_{1-4}$ alkyl, $C_{1-6}$ alkyl, $C_{1-6}$ alkoxy, and $C_{3-6}$ cycloalkyl, and when two substituents are contained, the two substituents can form a ring structure together with the carbon connected thereto; and the halogen atoms are selected from the group consisting of F, Cl and Br;

$R_2$ and $R_3$ are each independently selected from the group consisting of halogen atoms, and substituted or unsubstituted $C_{1-6}$ alkyl, the substituent being selected from the group consisting of halogen atoms, hydroxy, and $C_{1-6}$ alkoxy; and $R_1$ is selected from the group consisting of hydrogen, cyano, substituted or unsubstituted $C_{1-6}$ alkyl, and substituted or unsubstituted $C_{3-6}$ cycloalkyl, the substituent being selected from the group consisting of halogen atoms, hydroxy, and $C_{1-6}$ alkoxy;

comprising a step of contacting a compound of Formula (I-c):

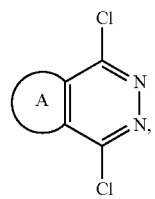

Formula (I-c)

or a salt thereof, with a compound of Formula (I-d):

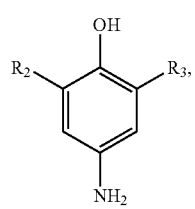

Formula (I-d)

or a salt thereof, to produce a compound of Formula (I-e):

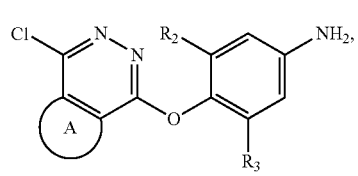

Formula (I-e)

or a salt thereof.

2. The method of claim 1, wherein the step of contacting the compound of Formula (I-c) with the compound of Formula (I-d) takes place in the presence of a base.

3. The method of claim 1, further comprising a step of subjecting the compound of Formula (I-e):

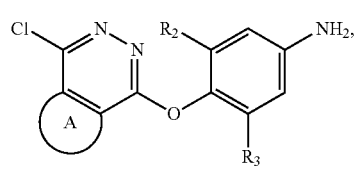

Formula (I-e)

or a salt thereof, to an alkaline or acidic environment at a high temperature to produce a compound of Formula (I-f):

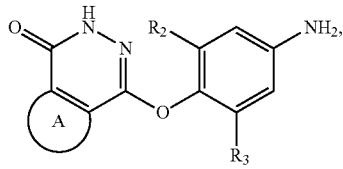

Formula (I-f)

or a salt thereof.

4. The method of claim 3, wherein the high temperature is greater than 100° C.

5. The method of claim 3, wherein the alkaline or acidic environment comprises acetic acid and sodium acetate.

6. The method of claim 3, wherein the alkaline environment comprises sodium hydroxide.

7. The method of claim 1, further comprising a step of contacting a compound of Formula (I-f):

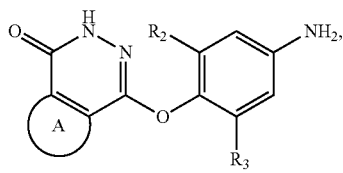

Formula (I-f)

or a salt thereof, with a compound of Formula I-g:

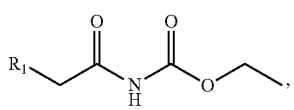

Formula (I-g)

or a salt thereof, to produce the compound of Formula (I):

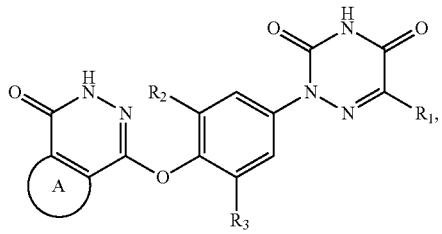

Formula (I)

or a salt thereof.

8. The method of claim 7, wherein the step of contacting the compound of Formula (I-f), or a salt thereof, with the compound of Formula (I-g), or a salt thereof, takes place in the presence of a nitrite, in an acidic aqueous solution.

9. The method of claim 8, wherein the nitrite is sodium nitrite.

10. The method of claim 7, wherein the acidic aqueous solution comprises hydrochloric acid.

11. The method of claim 7, wherein the method further comprises contacting with acetic acid and sodium acetate.

12. The method of claim 1, wherein the compound of Formula (I) is a compound of Formula (II):

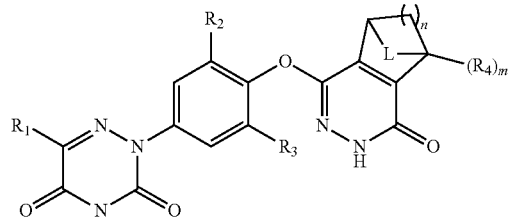

(II)

wherein, $R_2$ and $R_3$ are each independently selected from the group consisting of halogen atoms and substituted or unsubstituted $C_{1-6}$ alkyl, the substituent being selected from the group consisting of halogen atoms, hydroxy, and $C_{1-6}$ alkoxy; and $R_1$ is selected from the group consisting of hydrogen, cyano, substituted or unsubstituted $C_{1-6}$ alkyl, and substituted or unsubstituted $C_{3-6}$ cycloalkyl, the substituent being selected from the group consisting of halogen atoms, hydroxy, and $C_{1-6}$ alkoxy;

L is not present or is selected from the group consisting of —$CH_2$— and —$CH_2CH_2$—;

$R_4$ is selected from the group consisting of hydrogen, halogen atoms, hydroxy, —$OCF_3$, —$NH_2$, —$NHC_{1-4}$ alkyl, —$N(C_{1-4}$ alkyl$)_2$, $C_{1-6}$ alkyl, $C_{1-6}$ alkoxy, and $C_{3-6}$ cycloalkyl;

n is an integer from the range 1 to 4;

m is an integer from the range 1 to 4;

when L is not present, the ring may have two or more substituents $R_4$ thereon; and the halogen atoms are selected from the group consisting of F, Cl, and Br.

13. The method of claim 12, wherein:

$R_4$ is selected from the group consisting of hydrogen and $C_{1-3}$ alkyl;

L is not present;

n is 1, 2 or 3; and m is 1 or 2.

14. The method of claim 12, wherein:

$R_4$ is selected from the group consisting of hydrogen and $C_{1-3}$ alkyl;

L is —$CH_2$— or —$CH_2CH_2$—;

n is 1, 2 or 3; and m is 1 or 2.

15. The method of claim 1, wherein Ring A is a $C_{5-10}$ aromatic ring optionally substituted with one or more substituents independently selected from the group consisting of hydrogen, halogen atoms, hydroxy, —$OCF_3$, —$NH_2$, —$NHC_{1-4}$ alkyl, —$N(C_{1-4}$alkyl$)_2$, —$CONH_2$, —$CONHC_{1-4}$ alkyl, —$CON(C_{1-4}$ alkyl$)_2$, —$NHCOC_{1-4}$ alkyl, $C_{1-6}$ alkyl, $C_{1-6}$ alkoxy, and $C_{3-6}$ cycloalkyl, and when two substituents are contained, the two substituents can form a ring structure together with the carbon connected thereto; and the halogen atoms are selected from the group consisting of F, Cl, and Br.

16. The method of claim 15, wherein the compound of Formula (I) is a compound of Formula (III):

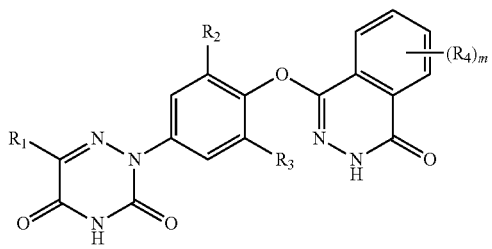

wherein:
- R$_2$ and R$_3$ are each independently selected from the group consisting of halogen atoms and substituted or unsubstituted C$_{1-6}$ alkyl, the substituent being selected from the group consisting of halogen atoms, hydroxy, and C$_{1-6}$ alkoxy; and
- R$_1$ is selected from the group consisting of hydrogen, cyano, substituted or unsubstituted C$_{1-6}$ alkyl, and substituted or unsubstituted C$_{3-6}$ cycloalkyl, the substituent being selected from the group consisting of halogen atoms, hydroxy, and C$_{1-6}$ alkoxy;
- R$_4$ is selected from the group consisting of hydrogen, halogen atoms, hydroxy, —OCF$_3$, —NH$_2$, —NHC$_{1-4}$ alkyl, —N(C$_{1-4}$ alkyl)$_2$, —CONH$_2$, —CONHC$_{1-4}$ alkyl, —CON(C$_{1-4}$ alkyl)$_2$, —NHCOC$_{1-4}$ alkyl, C$_{1-6}$ alkyl, C$_{1-6}$ alkoxy, and C$_{3-6}$ cycloalkyl;
- m is an integer from the range 1 to 4; and
- the halogen atoms are selected from the group consisting of F, Cl, and Br.

17. The method of claim 16, wherein R$_4$ is selected from the group consisting of hydrogen, halogen atoms, hydroxy, —OCF$_3$, C$_{1-6}$ alkyl, C$_{1-6}$ alkoxy, and C$_{3-6}$ cycloalkyl; and m is an integer from the range 1 to 3.

18. The method of claim 17, wherein R$_4$ is selected from the group consisting of hydrogen, halogen atoms, and C$_{1-3}$ alkyl; and m is 1 or 2.

19. The method of claim 18, wherein R$_4$ is hydrogen.

20. The method of claim 1, wherein the compound of Formula (I) is selected from the following compounds:

1

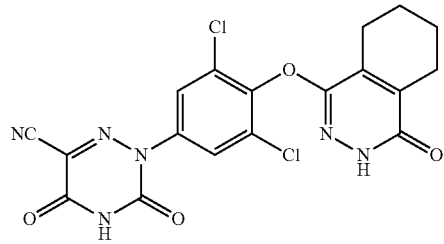

2

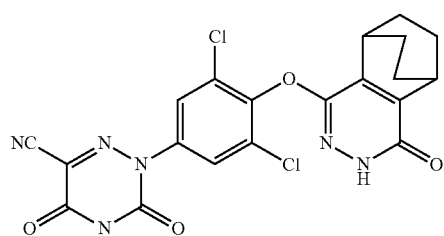

3

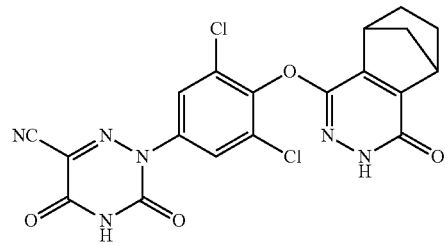

4

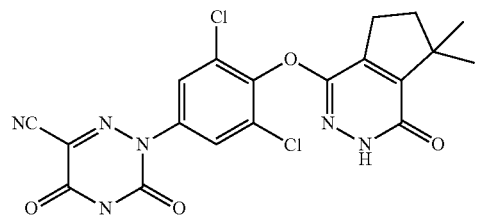

5

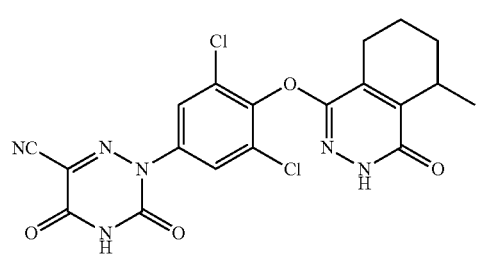

6

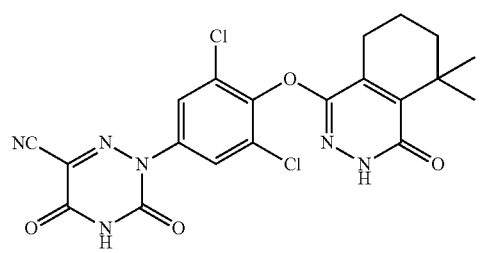

7

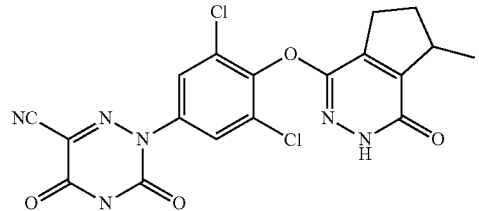

8

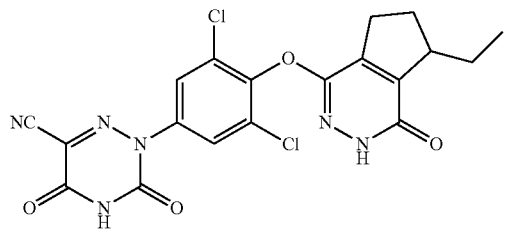

9
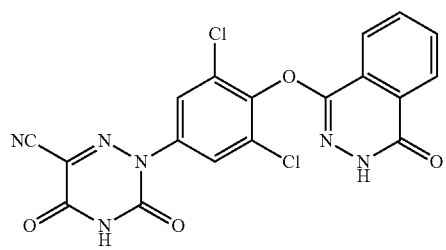
10
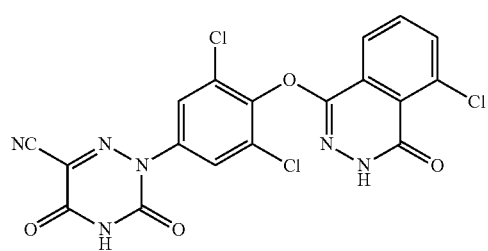
11
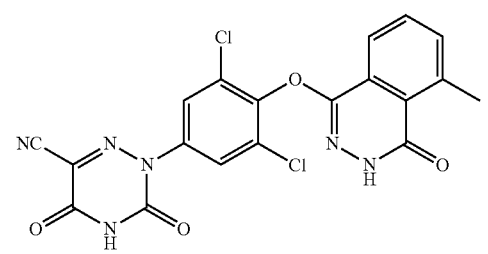
12
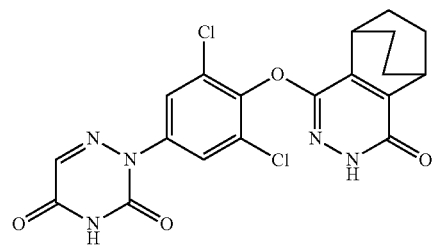
13
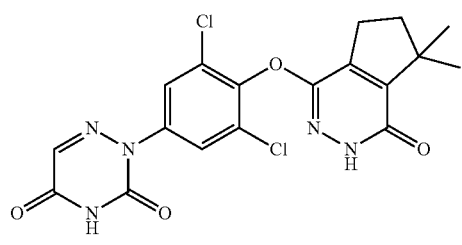
14
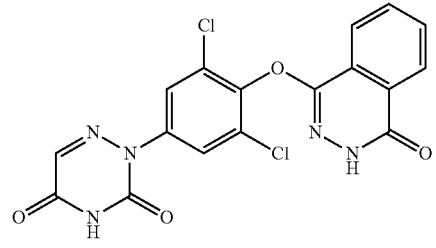
15
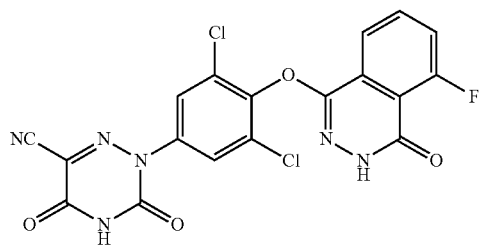
16
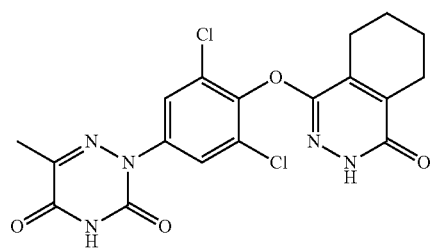
17
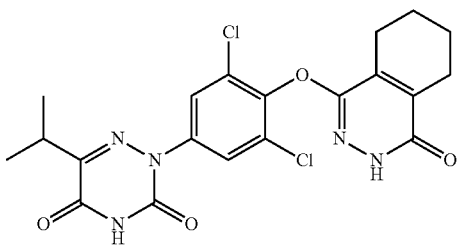
18
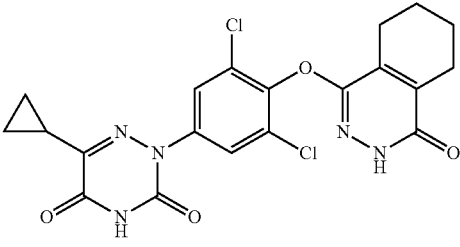
19
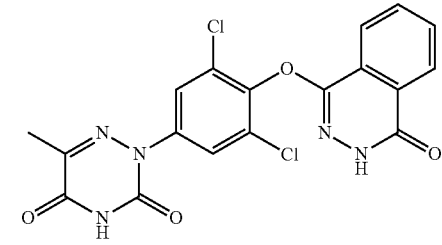
20
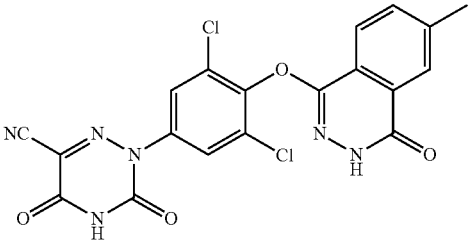

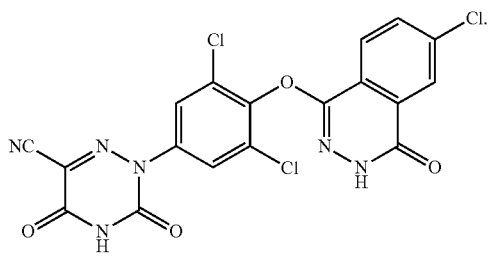
21. The method of claim 1, wherein the compound of Formula (I) is selected from the following compounds:
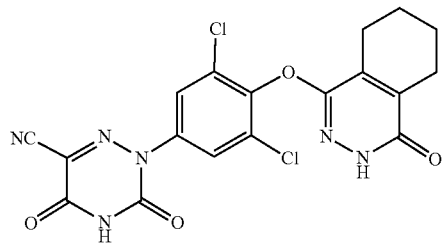
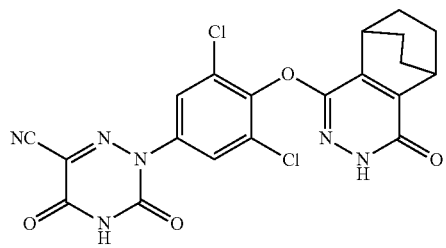
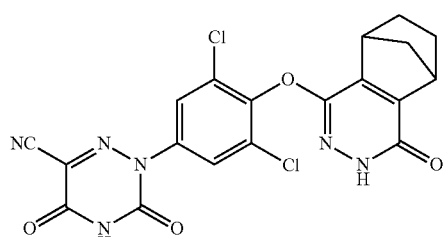
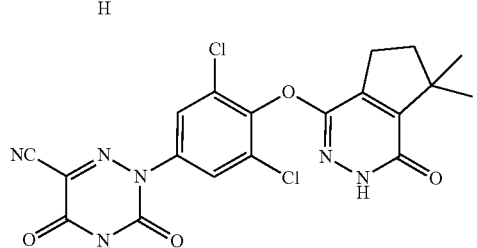
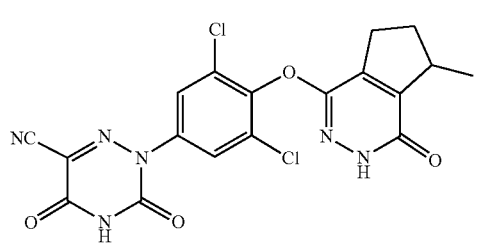
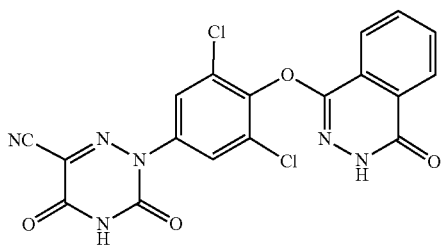
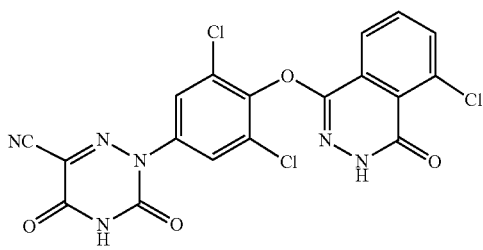
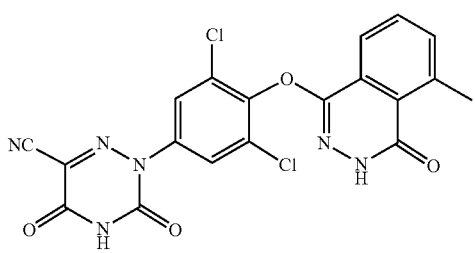
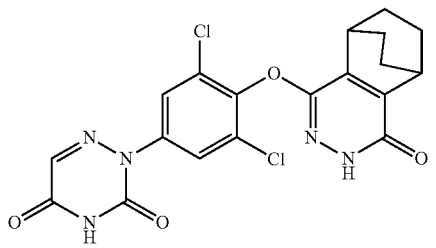
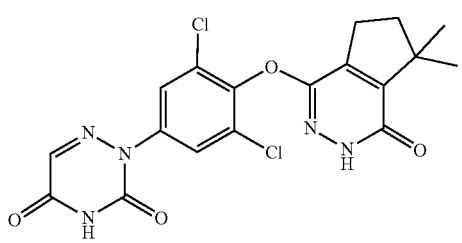
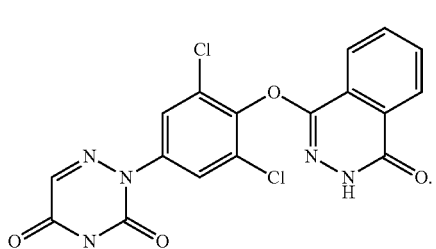
22. The method of claim 1, wherein the compound of Formula (I) is

23. The method of claim 1, wherein the compound of Formula (I) is
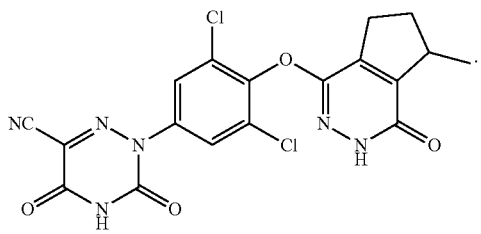
24. The method of claim 1, wherein the compound of Formula (I) is
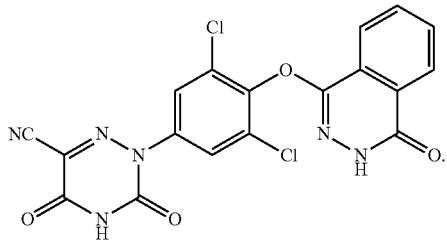
25. The method of claim 1, wherein the compound of Formula (I) is
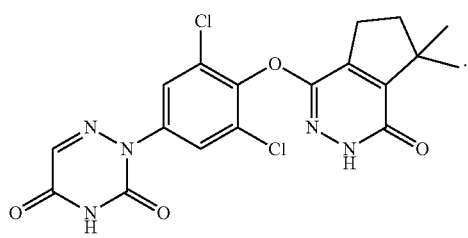
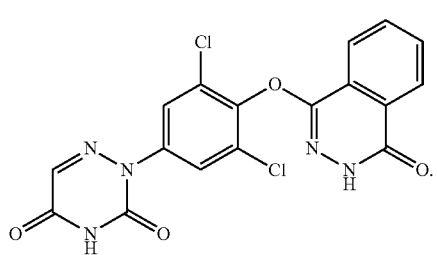
* * * * *

UNITED STATES PATENT AND TRADEMARK OFFICE
CERTIFICATE OF CORRECTION

Page 1 of 3

PATENT NO. : 12,338,232 B2
APPLICATION NO. : 18/315291
DATED : June 24, 2025
INVENTOR(S) : Shanghai Yu et al.

It is certified that error appears in the above-identified patent and that said Letters Patent is hereby corrected as shown below:

In the Specification

At Column 22, Line number 9, " 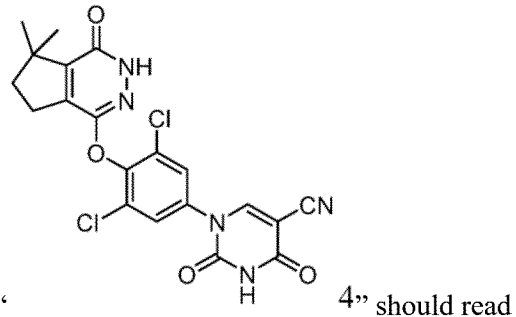 4" should read

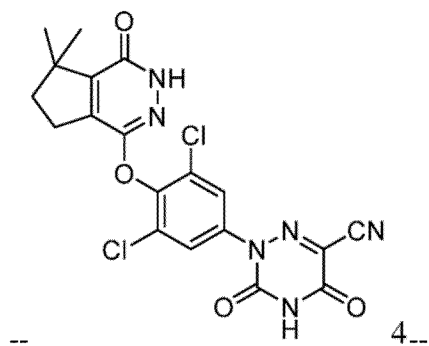 4--

Signed and Sealed this
Thirtieth Day of September, 2025

John A. Squires
*Director of the United States Patent and Trademark Office*

CERTIFICATE OF CORRECTION (continued)
U.S. Pat. No. 12,338,232 B2

At Column 24, Line number 34, " 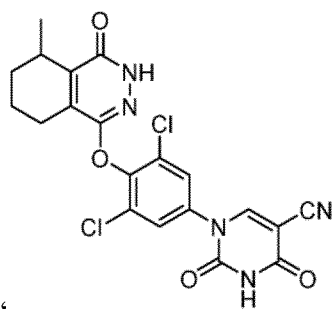 5" should read

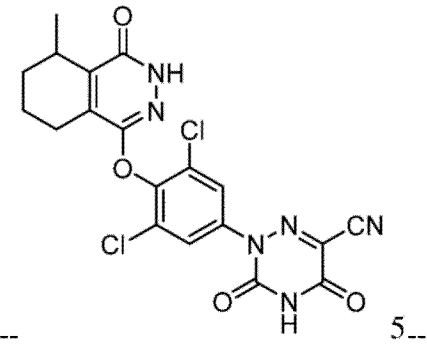 -- 5 --

At Column 27, Line number 9, " 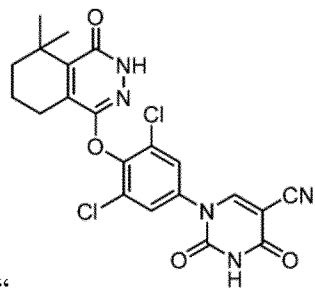 6" should read

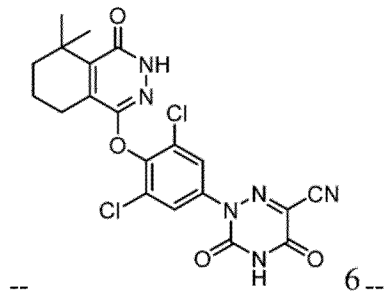 -- 6 --

At Column 27, Line number 43, " 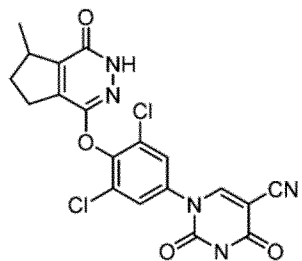 7" should read

CERTIFICATE OF CORRECTION (continued)
U.S. Pat. No. 12,338,232 B2

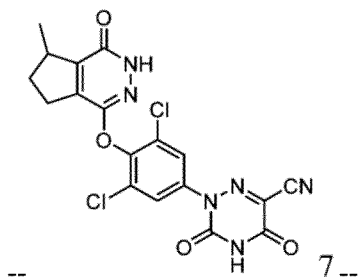 7 --

At Column 28, Line number 12, " 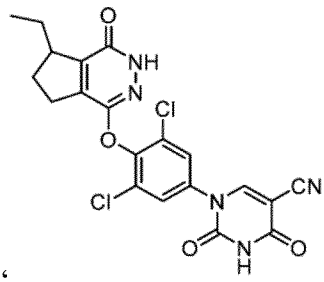 8" should read

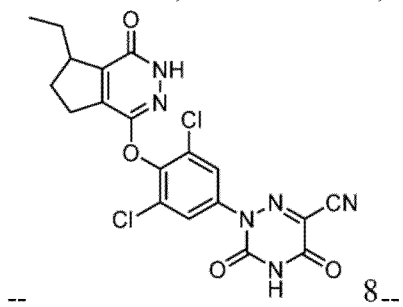 8 --